(12) United States Patent
Kulkarni et al.

(10) Patent No.: US 10,869,884 B2
(45) Date of Patent: Dec. 22, 2020

(54) CYCLODEXTRIN BASED POLYMERS, METHODS, COMPOSITIONS AND APPLICATIONS THEREOF

(71) Applicant: ATEN PORUS LIFESCIENCES, Karnataka (IN)

(72) Inventors: Aditya Kulkarni, Karnataka (IN); Atul Dolas, Karnataka (IN); Soniya Johny, Karnataka (IN); Princy Khurana, Karnataka (IN); Sandeep Goyal, Karnataka (IN)

(73) Assignee: ATEN PORUS LIFESCIENCES, Karnataka (IN)

( * ) Notice: Subject to any disclaimer, the term of this patent is extended or adjusted under 35 U.S.C. 154(b) by 0 days.

(21) Appl. No.: 16/334,290

(22) PCT Filed: Sep. 18, 2017

(86) PCT No.: PCT/IB2017/055627
§ 371 (c)(1),
(2) Date: Mar. 18, 2019

(87) PCT Pub. No.: WO2018/051298
PCT Pub. Date: Mar. 22, 2018

(65) Prior Publication Data
US 2019/0209605 A1 Jul. 11, 2019

(30) Foreign Application Priority Data

Sep. 19, 2016 (IN) .............................. 201641031941

(51) Int. Cl.
  *A61K 31/724* (2006.01)
  *C08B 37/16* (2006.01)
  *A61K 31/765* (2006.01)
  *A61K 47/54* (2017.01)
  *A61P 13/12* (2006.01)
  *A61K 45/06* (2006.01)

(52) U.S. Cl.
  CPC .......... *A61K 31/724* (2013.01); *A61K 31/765* (2013.01); *A61K 45/06* (2013.01); *A61K 47/54* (2017.08); *A61P 13/12* (2018.01); *C08B 37/0012* (2013.01)

(58) Field of Classification Search
None
See application file for complete search history.

(56) References Cited

U.S. PATENT DOCUMENTS

| 5,840,713 A | 11/1998 | Weisz |
| 2002/0151523 A1 | 10/2002 | Davis et al. |
| 2007/0238788 A1* | 10/2007 | Hauck ..................... A61P 13/10 514/578 |
| 2013/0005684 A1* | 1/2013 | Fichert .................... A61P 13/00 514/58 |
| 2015/0065457 A1* | 3/2015 | Fornoni .................... A61P 1/18 514/58 |
| 2015/0118318 A1* | 4/2015 | Fahmy ................. A61K 9/0019 424/498 |

FOREIGN PATENT DOCUMENTS

| DE | 10 2010 012282 A1 | 9/2011 |
| WO | WO 2014/022841 A1 | 2/2014 |
| WO | WO 2014/194250 A2 | 12/2014 |
| WO | WO 2017/125889 A1 | 7/2017 |

OTHER PUBLICATIONS

Bartlett, D. W., & Davis, M. E. (2007). Physicochemical and biological characterization of targeted, nucleic acid-containing nanoparticles. Bioconjugate chemistry, 18(2), 456-468. (Year: 2007).*
Zuckerman, J. E., Gale, A., Wu, P., Ma, R., & Davis, M. E. (2015). siRNA delivery to the glomerular mesangium using polycationic cyclodextrin nanoparticles containing siRNA. Nucleic acid therapeutics, 25(2), 53-64. (Year: 2015).*
Rahman, M., & Smith, M. C. (1998). Chronic renal insufficiency: a diagnostic and therapeutic approach. Archives of Internal medicine, 158(16), 1743-1752. (Year: 1998).*
Merscher-Gomez, et al., "Cyclodextrin Protects Podocytes in Diabetic Kidney Disease," *Diabetes*, vol. 62, pp. 3817-3827 (Nov. 2013).
Pedigo, et al., "Local TNF causes NFATc1-dependent Cholesterol-Mediated Podocyte Injury," *The Journal of Clinical Investigation*, vol. 126, No. 9, pp. 3336-3350 (Sep. 2016).
Zhang et al., "A review of recent applications of cyclodextrins for drug discovery," *Exp. Opin. Ther. Patients*, vol. 9, No. 12, pp. 1697-1717 (1999).

\* cited by examiner

*Primary Examiner* — Dale R Miller
(74) *Attorney, Agent, or Firm* — Foley & Lardner LLP

(57) ABSTRACT

The present disclosure relates to polymers comprising conjugates of cyclodextrin or derivatives thereof and a linker moiety, and their application in treating lipid storage disorders by the removal of lipids such as cholesterol from cells. The polymers having the following structure: Formula (I), wherein CD, L, and n are defined herein, exhibit improved properties including but not limited to improved biocompatibility, improved retention time, prolonged duration of action in cells, and increased efficacy in treating a variety of kidney diseases and associated conditions.

19 Claims, 16 Drawing Sheets

R=H, β-Cyclodextrin;
R=CH$_2$CH(OH)CH$_3$, Hydroxy propyl β-Cyclodextrin;

CYCLODEXTRIN BASED POLYMERS, METHODS, COMPOSITIONS AND APPLICATIONS THEREOF

PRIORITY INFORMATION

This application is the U.S. National Stage of PCT/IB2017/055627, filed Sep. 18, 2017, which claims priority from India Patent Application No. 201641031941, filed Sep. 19, 2016, the contents of which are incorporated herein by reference in their entirety.

TECHNICAL FIELD

The present disclosure is in the field of biomedical, pharmaceutical and polymeric sciences. The present disclosure relates macromolecular therapeutic agents, methods of making the same, and the therapeutic uses of the same in the treatment of various disorders including lipid storage and kidney disorders. In certain specific embodiments, the disclosure relates to polymers comprising conjugates of cyclodextrins, a salt thereof, a solvate thereof, and/or cyclodextrin derivatives, methods of making the same, and their use as therapeutic agents in the treatment of various disorders, for example removing excess lipids such as cholesterol from cells and/or treating lipid storage disorders.

BACKGROUND

Lipid storage diseases, or the lipidoses, are a group of metabolic disorders in which harmful or excessive amounts of lipids (e.g., cholesterol) accumulate in various cells and tissues in the body. Patients with these disorders typically exhibit elevated levels of cholesterol in various tissues of the body, as these patients either do not produce adequate quantities of one or more enzymes needed to metabolize lipids or they produce enzymes that do not work properly. In recent years, sedentary life styles and poor dietary habits of people are also factors leading to lipid over accumulation in patient tissues.

Overexpression or accumulation of lipids in animal tissue is a major health factor associated with a variety of diseases. For example, it is well established that elevated plasma cholesterol levels and, in particular, low-density lipoprotein (LDL) cholesterol levels, can play an important role in the development of coronary heart disease, stroke, peripheral vascular disease, kidney disease, atherosclerosis, and hypertension. Renal accumulation of cholesterol in particular, has been correlated with the development of glomerular diseases such as Focal Segmental Glomerulosclerosis (FSGS), Diabetic Kidney Disease, and Alport Syndrome.

Focal Segmental Glomerulosclerosis is the leading cause of kidney failure in adults, and is responsible for approximately 17% of the cases of nephrotic syndrome. It is estimated that 50,000 cases of FSGS have been reported in the United States alone, with about 5,000 new cases reported annually. Treatment is currently limited to angiotensin-converting-enzyme (ACE) inhibitors and angiotensin receptor blockers (ARBs), but each of these options only delays disease progression. Dialysis and ultimately kidney transplantation are necessary, and even after transplantation FSGS returns in 30-40% of patients.

An emerging therapy for cholesterol-associated kidney diseases has been the administration of cholesterol-clearance molecules, such as cyclodextrin. Unfortunately, the current generation of cyclodextrin treatments undergo rapid clearance from the bloodstream of patients due to their small size. Therefore, to maintain a minimum effective concentration of a therapeutic drug, usually high concentrations/doses or repeated administration of these cholesterol-clearing drugs are required to be administered to the subject.

Since administration of higher concentrations/doses of the therapeutic agent/drug to the subject may lead to toxicity and adversely affect various organs of the subject, this approach is not a general solution to the drawbacks stemming from rapid clearance of current cyclodextrin-based treatments from the body. Hence, balancing the clearance rate of these therapeutic agents while maintaining a safe, minimum effective concentration of these drugs in the desired organ or tissue, without compromising the efficacy of the drug, remains both a challenge and a critical objective in the research and development of new drugs and drug delivery systems for treating cholesterol-associated kidney disease.

Accordingly, there has been a continuing need in the art to provide drugs such as drug-polymer conjugates that have an improved efficacy profile including a prolonged duration of action for treating lysosomal lipid storage disorders that result in glomerular kidney diseases. The subject matter described in the present disclosure overcomes the aforesaid drawbacks of the prior art.

SUMMARY OF THE DISCLOSURE

The polymers of the present disclosure are useful for treating a condition or a disease associated with abnormal lipid storage. In some embodiments, the present disclosure teaches a method for treating a kidney glomerular disease, said method comprising administering to a subject in need thereof, an effective amount of a cyclodextrin polymer having the following structure:

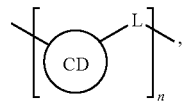

wherein

CD is a cyclodextrin moiety, or a derivative thereof;

L is a linker moiety; and n is from 4 to 1000.

In one embodiment of the present method, the cyclodextrin moiety is selected from α-cyclodextrin, β-cyclodextrin, γ-cyclodextrin, derivatives thereof, and combinations thereof.

In another embodiment of the present method, L comprises the following structure:

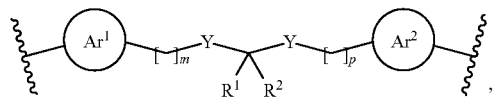

wherein
Ar[1] and Ar[2] are each independently a 5- or 6-membered heteroaryl comprising 1, 2, 3 or 4 heteroatoms individually selected from N, O, and S, wherein Ar[1] and Ar[2] are optionally substituted with $R^3$;
Y is independently O, S, or $NR^4$;
m and p are each independently an integer from 1 to 10;
$R^1$ and $R^2$ are each independently $R^4$, $OR^4$, $SR^4$ or $R^1$ and $R^2$ taken together with the carbon to which they are attached form a double bonded O, S, or $NR^4$, each of which are optionally substituted; and
$R^3$ is selected from $C_1$-$C_3$ alkyl, $C_1$-$C_3$ alkyl sulfide, hydrazone, amine, and halogen.
$R^4$ is H or a saturated or unsaturated $C_1$-$C_{10}$ linear alkyl, saturated or unsaturated $C_1$-$C_{10}$ branched alkyl, or saturated or unsaturated $C_1$-$C_{10}$ cycloalkyl, each of which is optionally substituted.

In specific embodiments of the present method, L is

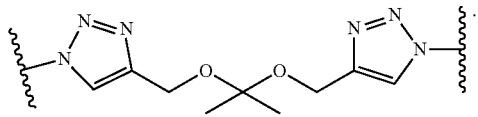 [SMILES: *n1cc(COC(C)(C)OCc2cn(*)nn2)nn1]

In one embodiment of the present method, a polymer for treating a condition or a disease associated with abnormal lipid storage such as kidney glomerular disease comprising 4 to 1000 cyclodextrin units has the following structure:

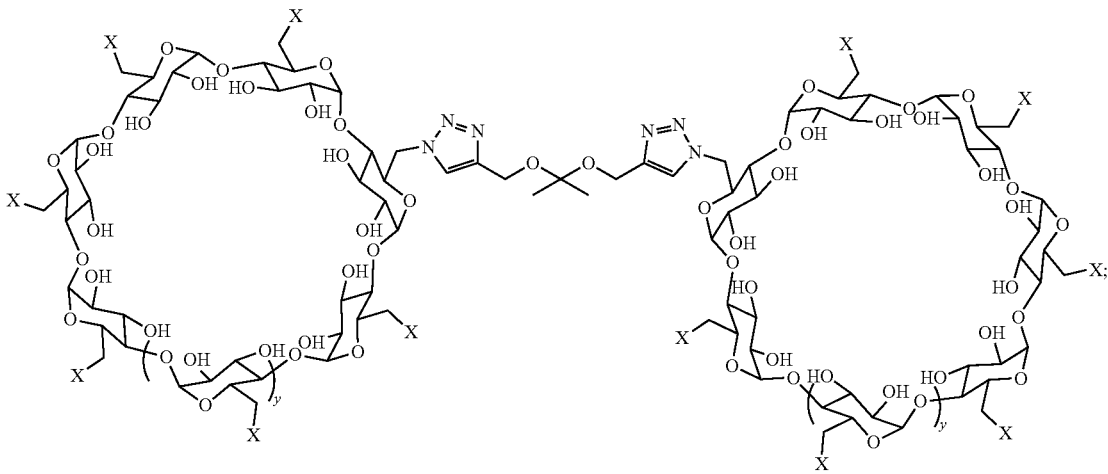

wherein X is OH, except that at least one X from each cyclodextrin subunit is optionally substituted by:

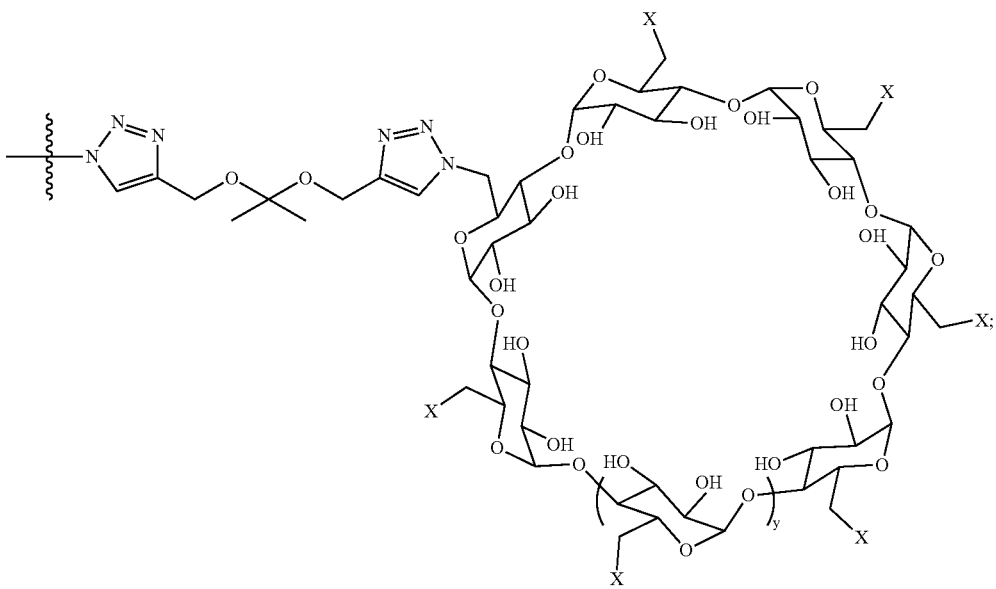

and wherein y is 0, 1, or 2.

In another embodiment of the present method, a polymer of the present disclosure for treating a condition or a disease associated with abnormal lipid storage has the following structure:

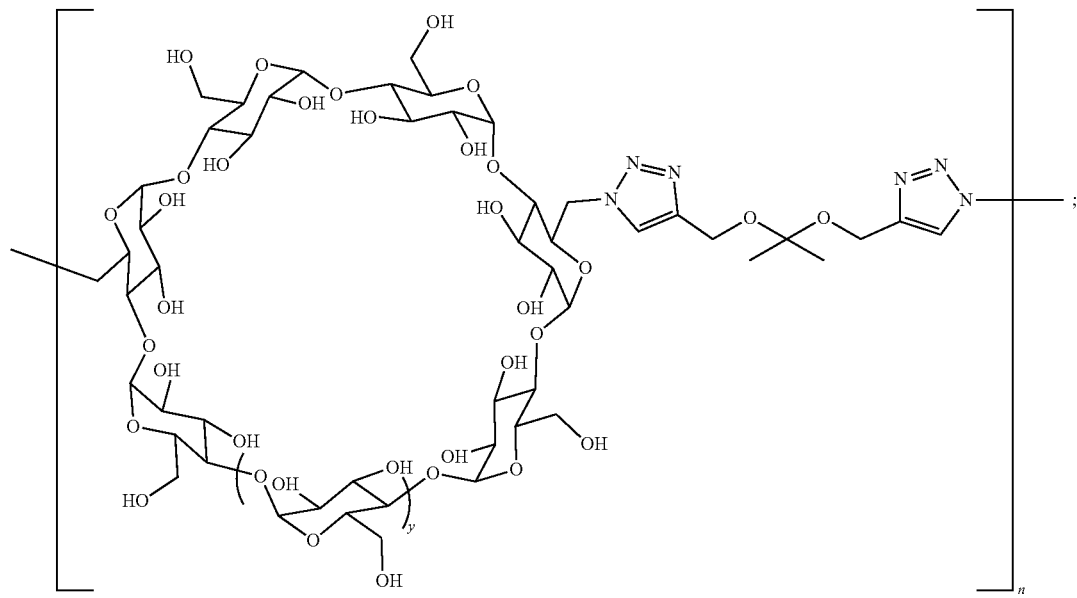

wherein y is 0, 1, or 2, and n is from 4 to 1000.

In specific embodiments of the present method, y is 0. In other specific embodiments, y is 1. In still other specific embodiments, y is 2

In one embodiment of the present disclosure, methods of treatment are provided using a pharmaceutical composition comprising a pharmaceutically acceptable carrier or a pharmaceutical excipient and a polymer of the present disclosure, e.g., polymers of cyclodextrin conjugates (pBCDKs). In another embodiment, the pharmaceutical composition disclosed herein further comprises one or more additional therapeutically active agents. In related embodiments, the one or more additional therapeutically active agents are selected from the group consisting of angiotensin-converting-enzyme (ACE) inhibitors and angiotensin receptor blockers (ARBs). In various embodiments, the one or more additional therapeutically active agents are selected from the group consisting of angiotensin-converting-enzyme (ACE) inhibitors. In specific embodiments, the one or more ACE inhibitors are selected from the group consisting of captopril, zofenopril. enalapril, ramipril, quinapril, perindopril, lisinopril, benazepril, imidapril, trandolapril, cilazapril, and fosinopril. In a specific embodiment, the one or more ACE inhibitors is ramipril. In various other embodiments, the one or more additional therapeutically active agents are selected from the group consisting of angiotensin receptor blockers (ARBs). In specific embodiments, the one or more ARBs are selected from the group consisting of azilsartan, candesartan, eprosartan, irbesartan, losartan, olmesartan, telmisartan, sparsentan, and valsartan. In a specific embodiment, the one or more ARBs is sparsentan.

In various embodiments, the polymers and compositions of the present disclosure are useful in treating lipid storage diseases (lipidoses). In other various embodiments, the polymers and compositions of the present disclosure are useful in treating lipid storage diseases that result from the production of insufficient amounts of enzymes needed to metabolize lipids or the production of enzymes lacking proper function.

In some embodiments, the polymer conjugates (pBCDKs) and compositions are useful in treating lipid storage diseases that can result from elevated plasma cholesterol (e.g. low-density lipoproteins) levels such as coronary heart disease, stroke, peripheral vascular disease, kidney disease, atherosclerosis, and hypertension. In other related embodiments, the pBCDKs and compositions of the present invention are useful in treating kidney diseases that are glomerular diseases selected from the group consisting of: Focal Segmental Glomerulosclerosis, Alport Syndrome, Diabetic Kidney Disease, Minimal Change Kidney Disease, and Minimal Change Nephropathy.

In some embodiments, the present disclosure provides a method for reducing lipid content in cells, a plasma membrane of cells or tissues in a patient suffering from a glomerular disease, said method comprising administering to the patient an effective amount of a cyclodextrin polymer that reduces cellular lipid content. In some embodiments, the reducing is a removal of excess lipid from cells, a plasma membrane of cells, or tissues in said patient. The cyclodextrin polymers used for the treatment methods of the present disclosure are further described below.

In one embodiment of the present disclosure, a method of treating lipid storage disorder is provided comprising administering to a subject in need thereof a polymer of the present disclosure, e.g., polymers of cyclodextrin conjugates (pBCDKs).

DETAILED DESCRIPTION OF THE DISCLOSURE

Figure 1:
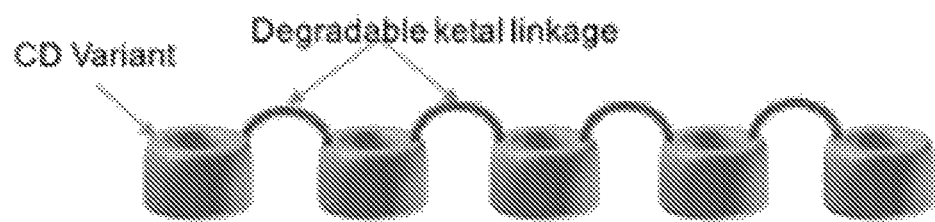
FIG. 1 is a drawing of the structure of an illustrative polymer comprising repeating units of cyclodextrin/cyclodextrin variants attached through linker moiety.
Figure 2:
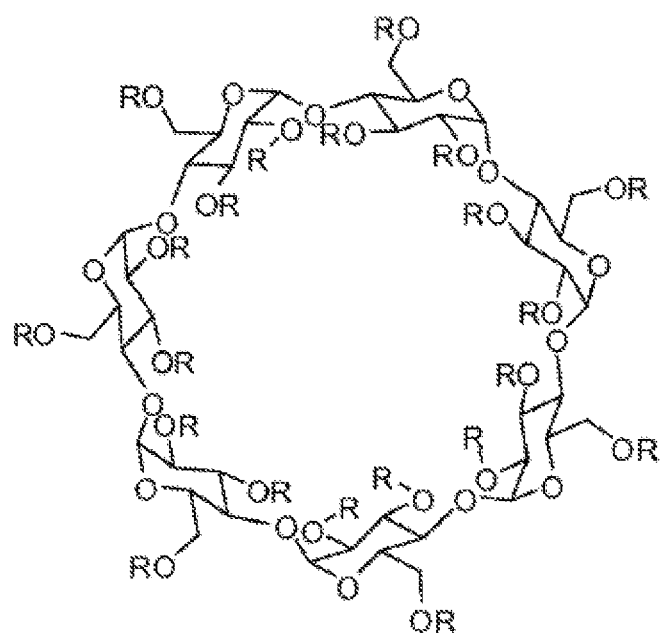
FIG. 2 depicts β-cyclodextrin (CD) and Hydroxypropyl-β-cyclodextrin (HP-β-CD).

While the following terms are believed to be well understood by one of ordinary skill in the art, the following definitions are set forth to facilitate explanation of the presently disclosed subject matter.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

Throughout the present specification, the terms "about" and/or "approximately" may be used in conjunction with numerical values and/or ranges. The term "about" is understood to mean those values near to a recited value. For example, "about 40 [units]" may mean within ±25% of 40 (e.g., from 30 to 50), within±20%, ±15%, ±10%, ±9%, ±8%, ±7%, ±6%, ±5%, ±4%, ±3%, ±2%, ±1%, less than±1%, or any other value or range of values therein or therebelow. In other contexts, the term "about" may refer to a value intermediate between adjacent values in a numerical sequence. Furthermore, the phrases "less than about [a value]" or "greater than about [a value]" should be understood in view of the definition of the term "about" provided herein. The terms "about" and "approximately" may be used interchangeably.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Reference throughout this specification to "one embodiment" or "an embodiment," etc. means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics can be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

As used herein in the claims, as well as in the specification, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively. See the United States Patent Office Manual of Patent Examining Procedures, Section 2111.03.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

As used herein, "substantially" or "substantial" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a composition that is "substantially free of" other active agents would either completely lack other active agents, or so nearly completely lack other active agents that the effect would be the same as if it completely lacked other active agents. In other words, a composition that is "substantially free of" an ingredient or element or another active agent may still contain such an item as long as there is no measurable effect thereof.

The terms below, as used herein, have the following meanings, unless indicated otherwise:

(a) "Amino" refers to the $NH_2$ radical.
(b) "Cyano" refers to the CN radical.
(c) "Halo" or "halogen" refers to bromo, chloro, fluoro or iodo radical.
(d) "Hydroxy" or "hydroxyl" refers to the OH radical.
(e) "Imino" refers to the =NH substituent.
(f) "Nitro" refers to the $NO_2$ radical.
(g) "Oxo" refers to the =O substituent.
(h) "Thioxo" refers to the =S substituent.

"Alkyl" or "alkyl group" refers to a fully saturated, straight or branched hydrocarbon chain radical having from one to twelve carbon atoms, and which is attached to the rest of the molecule by a single bond. Alkyls comprising any number of carbon atoms from 1 to 12 are included. An alkyl comprising up to 12 carbon atoms is a C1-C12 alkyl, an alkyl comprising up to 10 carbon atoms is a C1-C10 alkyl, an alkyl comprising up to 6 carbon atoms is a C1-C6 alkyl and an alkyl comprising up to 5 carbon atoms is a C1-C5 alkyl. A C1-C5 alkyl includes C5 alkyls, C4 alkyls, C3 alkyls, C2 alkyls and C1 alkyl (i.e., methyl). A C1-C6 alkyl includes all moieties described above for C1-C5 alkyls but also includes C6 alkyls. A C1-C10 alkyl includes all moieties described above for C1-C5 alkyls and C1-C6 alkyls, but also includes C7, C8, C9 and C10 alkyls. Similarly, a C1-C12 alkyl includes all the foregoing moieties, but also includes C11 and C12 alkyls. Non-limiting examples of C1-C12 alkyl include methyl, ethyl, n-propyl, i-propyl, sec-propyl, n-butyl, i butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, and having from one to twelve carbon atoms. Non-limiting examples of C1-C12 alkylene include methylene, ethylene, propylene, n butylene, ethenylene, propenylene, n butenylene, propynylene, n butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain radical having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a C2-C12 alkenyl, an alkenyl comprising up to 10 carbon atoms is a C2-C10 alkenyl, an alkenyl group comprising up to 6 carbon atoms is a C2-C6 alkenyl and an alkenyl comprising up to 5 carbon atoms is a C2-C5 alkenyl. A C2-C5 alkenyl includes C5 alkenyls, C4 alkenyls, C3 alkenyls, and C2 alkenyls. A C2-C6 alkenyl includes all moieties described above for C2-C5 alkenyls but also includes C6 alkenyls. A C2-C10 alkenyl includes all moieties described above for C2-C5 alkenyls and C2-C6 alkenyls, but also includes C7, C8, C9 and C10 alkenyls. Similarly, a C2-C12 alkenyl includes all the foregoing moieties, but also includes C11 and C12 alkenyls. Non-limiting examples of C2-C12 alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene" or "alkenylene chain" refers to a straight or branched divalent hydrocarbon chain radical, having from two to twelve carbon atoms, and having one or more carbon-carbon double bonds. Non-limiting examples of C2-C12 alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain radical having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a C2-C12 alkynyl, an alkynyl comprising up to 10 carbon atoms is a C2-C10 alkynyl, an alkynyl group comprising up to 6 carbon atoms is a C2-C6 alkynyl and an alkynyl comprising up to 5 carbon atoms is a C2-C5 alkynyl. A C2-C5 alkynyl includes C5 alkynyls, C4 alkynyls, C3 alkynyls, and C2 alkynyls. A C2-C6 alkynyl includes all moieties described above for C2-C5 alkynyls but also includes C6 alkynyls. A C2-C10 alkynyl includes all moieties described above for C2-C5 alkynyls and C2-C6 alkynyls, but also includes C7, C8, C9 and C10 alkynyls. Similarly, a C2-C12 alkynyl includes all the foregoing moieties, but also includes C11 and C12 alkynyls. Non-limiting examples of C2-C12 alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain radical, having from two to twelve carbon atoms, and having one or more carbon-carbon triple bonds. Non-limiting examples of C2-C12 alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

"Alkoxy" refers to a radical of the formula $OR_a$ where $R_a$ is an alkyl, alkenyl or alknyl radical as defined above containing one to twelve carbon atoms. Unless stated otherwise specifically in the specification, an alkoxy group can be optionally substituted.

"Alkylamino" refers to a radical of the formula —$NHR_a$ or —$NR_aR_a$ where each $R_a$ is, independently, an alkyl, alkenyl or alkynyl radical as defined above containing one to twelve carbon atoms. Unless stated otherwise specifically in the specification, an alkylamino group can be optionally substituted.

"Alkylcarbonyl" refers to the —C(=O)$R_a$ moiety, wherein $R_a$ is an alkyl, alkenyl or alkynyl radical as defined above. A non-limiting example of an alkyl carbonyl is the methyl carbonyl ("acetal") moiety. Alkylcarbonyl groups can also be referred to as "Cw-Cz acyl" where w and z depicts the range of the number of carbon in $R_a$, as defined above. For example, "C1-C10 acyl" refers to alkylcarbonyl group as defined above, where $R_a$ is C1-C10 alkyl, C1-C10 alkenyl, or C1-C10 alkynyl radical as defined above. Unless stated otherwise specifically in the specification, an alkyl carbonyl group can be optionally substituted.

"Aryl" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Aralkyl" or "arylalkyl" refers to a radical of the formula—$R_b$-$R_c$ where $R_b$ is an alkylene group as defined above and $R_c$ is one or more aryl radicals as defined above, for example, benzyl, diphenylmethyl and the like. Unless stated otherwise specifically in the specification, an aralkyl group can be optionally substituted.

"Aralkenyl" or "arylalkenyl" refers to a radical of the formula—$R_b$-$R_c$ where $R_b$ is an alkenylene o group as defined above and $R_c$ is one or more aryl radicals as defined above. Unless stated otherwise specifically in the specification, an aralkenyl group can be optionally substituted.

"Aralkynyl" or "arylalkynyl" refers to a radical of the formula —$R_b$-$R_c$ where $R_b$ is an alkynylene group as defined above and $R_c$ is one or more aryl radicals as defined above. Unless stated otherwise specifically in the specification, an aralkynyl group can be optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Carbocyclic rings include aryls and cycloalkyl, cycloalkenyl, and cycloalkynyl as defined herein. Unless stated otherwise specifically in the specification, a carbocyclyl group can be optionally substituted.

"Cycloalkyl" refers to a stable non aromatic monocyclic or polycyclic fully saturated hydrocarbon radical consisting solely of carbon and hydrogen atoms, which can include fused or bridged ring systems, having from three to twenty carbon atoms, preferably having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl bicyclo[2.2.1]heptanyl, and the like. Unless otherwise stated specifically in the specification, a cycloalkyl group can be optionally substituted.

"Heterocyclyl," "heterocyclic ring" or "heterocycle" refers to a stable 3 to 20 membered non aromatic ring radical which consists of two to twelve carbon atoms and from one to six heteroatoms selected from the group consisting of nitrogen, oxygen and sulfur. Heterocyclcl or heterocyclic rings include heteroaryls as defined below. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1 oxo thiomorpholinyl, and 1,1-dioxo thiomorpholinyl. Unless stated otherwise specifically in the specification, a heterocyclyl group can be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, an N-heterocyclyl group can be optionally substituted.

"Heteroaryl" refers to a 5 to 20 membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2 a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl 1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group can be optionally substituted.

"Heteroarylalkyl" refers to a radical of the formula $R_b$-$R_f$ where $R_b$ is an alkylene chain as defined above and $R_f$ is a heteroaryl radical as defined above. Unless stated otherwise specifically in the specification, a heteroarylalkyl group can be optionally substituted.

"Thioalkyl" refers to a radical of the formula —$SR_a$ where $R_a$ is an alkyl, alkenyl, or alkynyl radical as defined above containing one to twelve carbon atoms. Unless stated otherwise specifically in the specification, a thioalkyl group can be optionally substituted.

The term "substituted" used herein means any of the above groups (i.e., alkyl, alkylene, alkenyl, alkenylene, alkynyl, alkynylene, alkoxy, alkylamino, alkylcarbonyl, thioalkyl, aryl, aralkyl, carbocyclyl, cycloalkyl, cycloalkenyl, cycloalkynyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above sub stituents.

As used herein, the symbol

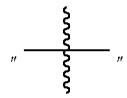

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

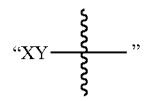

indicates that the chemical entity "XY" is bonded to another chemical entity via the point of attachment bond. Furthermore, the specific point of attachment to the non-depicted chemical entity can be specified by inference. For example, the compound $CH_3R^3$, wherein $R^3$ is H or

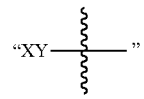

infers that when $R^3$ is "XY", the point of attachment bond is the same bond as the bond by which $R^3$ is depicted as being bonded to $CH_3$.

"Optional" or "optionally" means that the subsequently described event of circumstances can or cannot occur, and that the description includes instances where said event or circumstance occurs and instances in which it does not. For example, "optionally substituted aryl" means that the aryl radical can or cannot be substituted and that the description includes both substituted aryl radicals and aryl radicals having no substitution.

The term "treating" means one or more of relieving, alleviating, delaying, reducing, reversing, improving, or managing at least one symptom of a condition in a subject. The term "treating" may also mean one or more of arresting, delaying the onset (i.e., the period prior to clinical manifestation of the condition) or reducing the risk of developing or worsening a condition.

An "effective amount" means the amount of a formulation according to the invention that, when administered to a patient for treating a state, disorder or condition is sufficient to effect such treatment. The "effective amount" will vary depending on the active ingredient, the state, disorder, or condition to be treated and its severity, and the age, weight, physical condition and responsiveness of the mammal to be treated. In the context of therapeutic or prophylactic applications, in some embodiments, the amount of a composition administered to the subject will depend on the type, degree, and severity of the disease and on the characteristics of the individual, such as general health, age, sex, body weight and tolerance to drugs. The skilled artisan will be able to determine appropriate dosages depending on these and other factors.

The term "therapeutically effective" applied to dose or amount refers to that quantity of a compound or pharmaceutical formulation that is sufficient to result in a desired clinical benefit after administration to a patient in need thereof.

By "glomerular filtration rate" or GFR is meant the flow rate of filtered fluid through the kidney. In other words, it is the volume of fluid filtered from the renal (kidney) glomerular capillaries into the Bowman's capsule per unit time. GFR may be determined by a number of different techniques. For example, inulin or the inulin-analogon sinistrin may be injected into the plasma and its excretion in urine measured. As another example, GFR may be approximated based on determined (Ccr) or estimated (eCo) rate of creatinine clearance from the body using any convenient methodology. GFR in a normally functioning kidney is typically above 90 mL/min/1.73m$^2$ and no proteinuria By "proteinuria" is meant the presence of excessive amounts of serum proteinin in the urine. Proteinuria is a characteristic symptom of either renal (kidney), urinary, pancreatic distress, nephrotic syndromes (i.e., proteinuria larger than 3.5 grams per day), eclampsia, toxic lesions of kidneys, and it is frequently a symptom of diabetes mellitus. With severe proteinuria general hypoproteinemia can develop and it results in diminished oncotic pressure (ascites, edema, hydrothorax). Non-limiting examples of methods for detecting proteinuria include a urinalysis for protein, e.g. a quantitative protein determination in a timed urine collection or the ratio of protein levels relative to creatinine levels in a random urine collection, or by a foamy appearance or excessive frothing of the urine.

By "albuminuria" is meant a type of proteinuria in which the protein albumin is detectable in urine. Tests for albuminuria are typically more sensitive than tests for proteinuria. As such, in some instances, an individual may test positive for albuminuria but negative for proteinuria. Non-limiting examples of methods for measuring albuminuria include a quantitative albumin determination in a timed urine collection or the ratio of albumin levels relative to creatinine levels in a random urine collection (the albumin/creatinine ratio (ACR)).

By "normoalbuminuria" is meant having a substantially normal level of albumin in the urine. The presence and level of albumin protein in urine may be determined by a urine test, in which the concentration of albumin is measured in a 24-hour urine collection, or a spot test. Normoalbuminuria is characterized by a level of albumin of about 30 mg or less in a 24 hour collection (30 mg or less/day). In some instances, normoalbuminuria is defined based on the albumin/creatinine ratio (ACR), which is the amount of albumin in the sample compared to the concentration of creatinine in the sample. In such instances, normoalbuminuria is defined as an ACR of about 30 ug or less albumin / mg creatinine ("30 ug or less/mg").

By "microalbuminuria" is meant a condition caused by increased permeability for albumin in the renal glomerulus. Microalbuminuria is defined as a level of albumin of 30 to 300 mg in a 24 hour urine collection (30-300 mg/24 hours); or as an ACR of 30 to 300 µg albumin/mg creatinine ("30-300 µg/mg").

By "macroalbuminuria" is meant a condition caused by an abnormally high permeability for albumin in the renal glomerulus. Macroalbuminuria is characterized as a level of albumin of 300 mg or more in a 24 hour urine collection (more than 300 mg/24 hours); or as an ACR of 300 µg albumin nor more per mg creatinine ("300 µg or more/mg").

By "diabetes" is meant a metabolic disease that occurs when the pancreas does not produce enough of the hormone insulin to regulate blood sugar ("type 1 diabetes mellitus") or, alternatively, when the body cannot effectively use the insulin it produces ("type 2 diabetes mellitus"). Type 1 diabetes, also known as insulin dependent diabetes mellitus (IDDM), results from the destruction or dysfunction of β cells by the cells of the immune system. Symptoms include polyuria (frequent urination), polydipsia (increased thirst), polyphagia (increased hunger), and weight loss. T1D is fatal unless treated with insulin and must be continued indefinitely, although many people who develop the disease are otherwise healthy and treatment need not significantly impair normal activities. Exercising regularly, eating healthy foods and monitoring blood sugar may also be recommended. Other medications may be prescribed as well, including one or more of the following: medications to slow the movement of food through the stomach (e.g. pramlintide), high blood pressure medications, and cholesterol-lowering drugs. Type 2 diabetes, also known as non-insulin dependent diabetes mellitus (NIDDM), is associated with resistance to insulin in peripheral tissues (such as skeletal muscles and liver) and by a gradual decline in β cell function and numbers over time, as the β cells develop resistance to insulin as well. As a result, in T2D the pancreas does not make enough insulin to keep blood glucose levels normal. Symptoms include hyperglycemia (high blood sugar), diabetic ketoacidosis (increased ketones in urine), and hyperosmolar hyperglycemic nonketotic syndrome. Therapy may include blood sugar monitoring; healthy eating; regular exercise; diabetes medication that lowers glucose production (e.g. metformin, sitagliptin, saxagliptin, repaglinide, nateglinide, exenatide, liraglutide), that stimulates the pancreas to produce and release more insulin (e.g. glipizide, glyburide, glimepiride), and/or that blocks the action of enzymes that break down carbohydrates or make tissues more sensitive to insulin (e.g. pioglitazone); and insulin therapy.

"Diabetic kidney disease" and "Diabetic nephropathy" are used interchangeably herein to mean a chronic kidney disease caused by or associated with diabetes All weight percentages (i.e., "% by weight" and "wt. %" and w/w) referenced herein, unless otherwise indicated, are measured relative to the total weight of the pharmaceutical composition.

The following description includes information that may be useful in understanding the present invention. It is not an admission that any of the information provided herein is prior art or relevant to the presently claimed inventions, or that any publication specifically or implicitly referenced is prior art.

Methods of Using Cyclodextrin Polymers

The present disclosure addresses the aforementioned needs in the art and provides methods of using cyclodextrin based polymers including polymers of cyclodextrin conjugates (pBCDKs) as agents for drug therapy. The polymers of the present disclosure comprise repeating units of cyclodextrin moieties connected through linker moieties.

As used herein, the expressions "cyclodextrin based polymers", "polymers of cyclodextrin conjugates", "polymers comprising conjugates of cyclodextrins", "cyclodextrin: ketal conjugate", "cyclodextrin: ketal polymer", "cyclodextrin: ketal molecule", "conjugate of ketal with cyclodextrin", and "conjugate" are employed interchangeably within the instant disclosure and refer to the polymeric compound/therapeutic molecule/product of the instant disclosure.

In some embodiments, the present disclosure provides a method for treating kidney glomerular diseases, said method comprising administering to a subject in need thereof, an effective amount of a cyclodextrin polymer conjugate as described herein.

In various embodiments, the present methods provide compounds comprising the following structure:

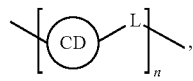

wherein
CD is a cyclodextrin moiety, or a derivative thereof;
L is a linker moiety; and
n is from 4 to 1000.

In another embodiment of the present methods, n is from 10 to 100. In one embodiment, n is from 10 to 75. In one embodiment, n is from 15 to 65. In one embodiment, n is from 20 to 30. In one embodiment, n is from 50 to 65. In one embodiment, n is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 100. In one specific embodiment, n is about 17. In another specific embodiment, n is about 25.

In one embodiment, the present method provides that the cyclodextrin moiety or a derivative thereof, is selected from α-cyclodextrin, β-cyclodextrin, γ-cyclodextrin, derivatives thereof, salts thereof, and combinations thereof. In some embodiments, the cyclodextrin moiety or a derivative thereof is a hydroxyalkyl-α-cyclodextrin, hydroxyalkyl-β-cyclodextrin, hydroxyalkyl-γ-cyclodextrin, derivatives thereof, salts thereof, or combinations thereof. In one embodiment, the alkyl in hydroxyalkyl-α-cyclodextrin, hydroxyalkyl-β-cyclodextrin, hydroxyalkyl-γ-cyclodextrin, derivatives thereof, a salt thereof, a solvate thereof, is selected from $C_1$-$C_{10}$ linear alkyl, $C_1$-$C_{10}$ branched alkyl or $C_1$-$C_{10}$ cycloalkyl, each optionally substituted. In some embodiments, the optional substituent for alkyl is selected from the group consisting of methyl, ethyl, and butyl. In still other embodiments of the present methods, the cyclodextrin, salt thereof, or combination thereof is an azidocyclodextrin or diazidocyclodextrin. In some embodiments, the diazidocyclodextrin is adiazido-α-cyclodextrin, diazido-β-cyclodextrin, or diazido-γ-cyclodextrin. In another embodiment of the present method, the azidocyclodextrin derivative is diazido-hydroxyalkyl-α-cyclodextrin, diazido-hydroxyalkyl-β-cyclodextrin, diazido-hydroxyalkyl-γ-cyclodextrin, or diazido-(2-hydroxypropy)-β-cyclodextrin. In still other embodiments of the present disclosure, the diazidocyclodextrin derivative is diazido-hydroxyalkyl-α-cyclodextrin, diazido-hydroxyalkyl-β-cyclodextrin, diazido-hydroxyalkyl-γ-cyclodextrin, diazido-(2-hydroxypropy)-β-cyclodextrin.

In a non-limiting embodiment of the present methods, the cyclodextrin moiety in the polymer of the present disclosure includes, but is not limited to, 3-cyclodextrin (β-CD), or its derivatives, wherein the derivatives are selected from the group consisting of α-cyclodextrin, hydroxypropyl β-cyclodextrin (HP-β-CD), sulfobutyl ether β-cyclodextrin (SBE-β-CD), methyl β-cyclodextrin (Me-β-CD), γ-cyclodextrin, and other charged or uncharged derivatives of β-CD.

In other embodiments, the present methods provide a cyclodextrin moiety or a derivative thereof that is derived from β-cyclodextrin, (2-hydroxypropy)-β-cyclodextrin, derivatives thereof, or combinations thereof. In one embodiment, the cyclodextrin is β-cyclodextrin or (2-hydroxypropy)-β-cyclodextrin.

The present methods particularly provide a polymer comprising a cyclodextrin-linker conjugate (pBCDK). In another embodiment of the present methods, the aforementioned polymer of cyclodextrin-linker conjugate comprises repeating units of β-cyclodextrin or its derivatives conjugated through a covalent linker moiety. In some embodiments, the cyclodextrin moiety, or a derivative thereof is derived from the reaction of a cyclodextrin or cyclodextrin derivative such as a hydroxyalkyl-α-cyclodextrin, hydroxyalkyl-β-cyclodextrin, hydroxyalkyl-γ-cyclodextrin, derivatives thereof, or combinations thereof with a linker as described herein.

As generally defined above, each L is independently a linker moiety. The linker serves to join one or more cyclodextrin subunits to one or more other cyclodextrin subunits in a way that provides a polymer of the present disclosure. In some embodiments, the present methods provide a linker that is covalently bound to the cyclodextrin. In various embodiments, the polymers of the present disclosure may be represented as:

─⎡cyclodextrin-linker⎤─$_n$ (e.g. FIG. 1).

In a non-limiting embodiment of the present method, the linker employed in the conjugate is a bio-degradable linker. In other non-limiting embodiments, the linker employed in the conjugate is a non-biodegradable linker. .

In one embodiment of the present method, a linker L comprises the following structure:

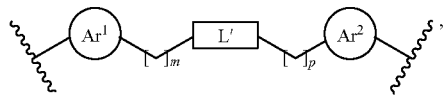

wherein

is selected from the group consisting of ketal, acetal, vinyl ether, ester, amide, urea, hydrazone, sulfoxide, sulfone, sulfonamide, carbonate, carbamate, thiocarbamate, imine, amidine, and guanidine;

Ar¹ and Ar² are each independently a 5- or 6-membered heteroaryl comprising 1, 2, 3 or 4 heteroatoms individually selected from N, O, and S, wherein Ar¹ and Ar² are optionally substituted with R³;

R³ is selected from $C_1$-$C_3$ alkyl, $C_1$-$C_3$ alkyl sulphide, hydrazone, amine, and halogen; and m and p is each independently an integer from 1 to 10.

In a related embodiment, the present methods provide Ar¹ and Ar² that are each 5-membered heteroaryl rings comprising 2 or 3 heteroatoms. In related embodiments, the 5-membered heteroaryl rings comprising 2 or 3 heteroatoms are selected from, but not limited to, oxazole, thiazole, imidazole, isoxazole, pyrrazole, triazole, thiadiazole, and oxadiazole. In a more specific embodiment, Ar¹ and Ar² are each triazole. In another embodiment, Ar¹ and Ar² are each tetrazole. In another embodiment, Ar¹ and Ar² are each 6-membered heteroaryl rings comprising 2 or 3 heteroatoms. In related embodiments, the 6-membered heteroaryl rings comprising 2 or 3 heteroatoms are selected from, but not limited to, pyrazine, pyrimidine, pyridazine, and triazine.

In another embodiment of the present method, a linker L provided by the present method comprises the following structure:

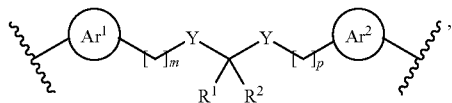

wherein

Ar¹ and Ar² are each independently a 5- or 6-membered heteroaryl comprising 1, 2, 3 or 4 heteroatoms individually selected from the group consisting of N, O, and S, wherein Ar¹ and Ar² are optionally substituted with R³;

Y is O, S, or NR⁴;

m and p is each independently an integer from 1 to 10;

R¹ and R² are each independently R⁴, OR⁴, SR⁴ or R¹ and R² together form a double bonded O, S, or NR⁴; and R³ is selected from the group consisting of $C_1$-$C_3$ alkyl, $C_1$-$C_3$ alkyl sulfide, hydrazone, amine, and halogen.

R⁴ is H or a saturated or unsaturated $C_1$-$C_{10}$ linear alkyl, saturated or unsaturated $C_1$-$C_{10}$ branched alkyl, or saturated or unsaturated $C_1$-$C_{10}$ cycloalkyl, each of which are optionally substituted.

In one embodiment, Y is O.

In one embodiment of the disclosed methods, m and p are each independently 1, 2, 3, 4, 5, 6, 7, 8, 9, or 10. In one embodiment, m is 1. In one embodiment, m is 2. In one embodiment, m is 3. In one embodiment, m is 4. In one embodiment, m is 5. In one embodiment, m is 6. In one embodiment, m is 7. In one embodiment, m is 8. In one embodiment, m is 9. In one embodiment, m is 10. In one embodiment, p is 1. In one embodiment, p is 2. In one embodiment, p is 3. In one embodiment, p is 4. In one embodiment, p is 5. In one embodiment, p is 6. In one embodiment, p is 7. In one embodiment, p is 8. In one embodiment, p is 9. In one embodiment, p is 10. In some embodiments, m and p are both 1.

In one embodiment of the present methods, R¹ and R² are each C1-C6 alkyl. In some embodiments, R¹ and R² are each C1-C3 alkyl. In one embodiment R¹ and R² are each selected form methyl, ethyl, propyl, and isopropyl. In one embodiment, wherein R¹ and R² are each methyl.

In another embodiment, the present methods provide Ar¹ and Ar² that are each 5-membered heteroaryl rings comprising 2 or 3 heteroatoms. In related embodiments, the 5-membered heteroaryl rings comprising 2 or 3 heteroatoms are selected from, but not limited to, oxazole, thiazole, imidazole, isoxazole, pyrrazole, triazole, thiadiazole, and oxadiazole. In a more specific embodiment, Ar¹ and Ar² are each triazole. In another embodiment, Ar¹ and Ar² are each tetrazole. In another embodiment, Ar¹ and Ar² are each 6-membered heteroaryl rings comprising 2 or 3 heteroatoms. In related embodiments, the 6-membered heteroaryl rings comprising 2 or 3 heteroatoms are selected from, but not limited to, pyrazine, pyrimidine, pyridazine, and triazine.

In one embodiment, Ar¹ and Ar² are the same heteroaryl.

In another embodiment of the present methods, the linker L comprises the following structure:

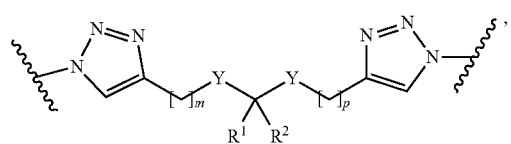

wherein

Y is O, S, or NR⁴;

m and p is each independently an integer from 1 to 10;

R¹ and R² are each independently R⁴, OR⁴, SR⁴ or R¹ and R² together form a double bonded O, S, or NR⁴; and R³ is selected from $C_1$-$C_3$ alkyl, $C_1$-$C_3$ alkyl sulphide, hydrazone, amine, and halogen.

R⁴ is H or a saturated or unsaturated $C_1$-$C_{10}$ linear alkyl, saturated or unsaturated $C_1$-$C_{10}$ branched alkyl, or saturated or unsaturated $C_1$-$C_{10}$ cycloalkyl, each of which are optionally substituted.

In some embodiments of the present method, m and p are each independently 1, 2, 3, 4, or 5. In other embodiments, m and p are both 1.

In one embodiment, the present methods provide R¹ and R² that are each C1-C6 alkyl.

In some embodiment, R¹ and R² are each C1-C3 alkyl. In one embodiment R¹ and R² are each selected form methyl, ethyl, propyl, and isopropyl. In one embodiment, wherein R¹ and R² are each methyl.

In another embodiment, the linker L of the present method comprises the following structure:

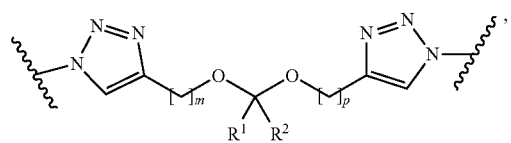

wherein m and p are each independently an integer from 1 to 10;

R¹ and R² are each independently R⁴, OR⁴, SR⁴ or R¹ and R² together form a double bonded O, S, or NR⁴; and R³ is selected from $C_1$-$C_3$ alkyl, $C_1$-$C_3$ alkyl sulfide, hydrazone, amine, and halogen.

$R^4$ is H or a saturated or unsaturated $C_1$-$C_{10}$ linear alkyl, saturated or unsaturated $C_1$-$C_{10}$ branched alkyl, or saturated or unsaturated $C_1$-$C_{10}$ cycloalkyl, each of which are optionally substituted.

In some embodiments, m and p are each independently 1, 2, 3, 4, 5, 6, 7, 8, 9, or 10. In other embodiments, m and p are both 1.

In one embodiment of the present method, $R^1$ and $R^2$ are each C1-C6 alkyl. In some embodiment, $R^1$ and $R^2$ are each C1-C3 alkyl. In one embodiment $R^1$ and $R^2$ are each selected form methyl, ethyl, propyl, and isopropyl. In one embodiment, wherein $R^1$ and $R^2$ are each methyl.

In one specific embodiment, the linker L disclosed by the method is

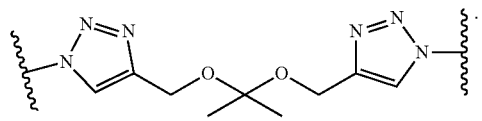 [SMILES: *n1cc(COC(C)(C)OCc2cn(*)nn2)nn1]

The present method more particularly relates to polymers of cyclodextrin-triazole-ketal-triazole conjugates. In one embodiment, a polymer of the present disclosure comprising 4 to 1000 cyclodextrin units has the following structure:

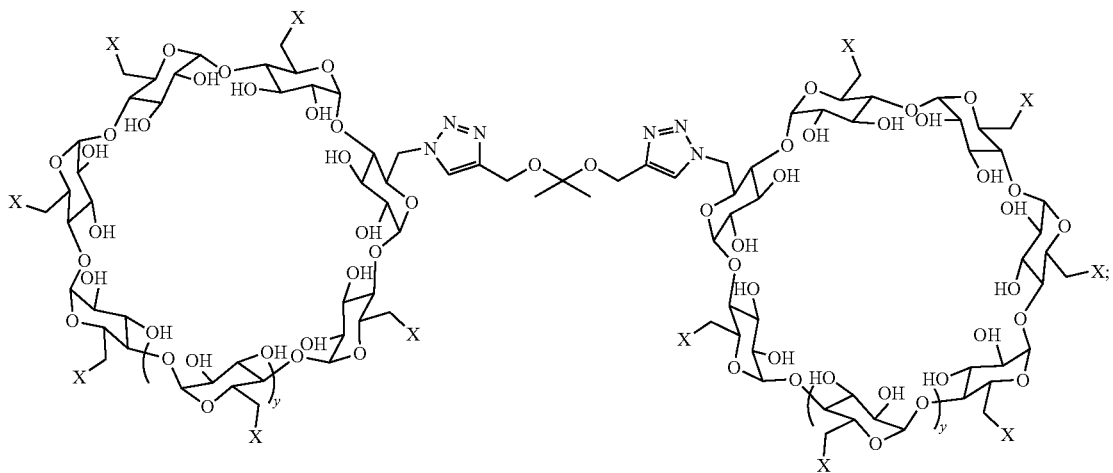

wherein X is OH, except that at least one X from each cyclodextrin subunit is optionally substituted by:

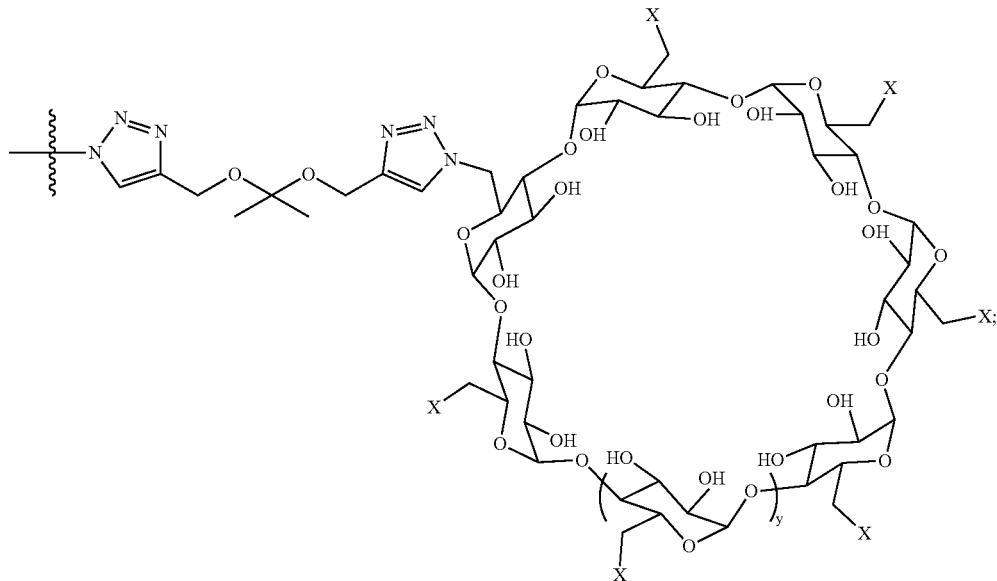

and wherein y is 0, 1, or 2.

In some embodiments y is 0. In other embodiments, y is 1. In still other embodiments, y is 2.

In another embodiment of the present method, the polymer of the present disclosure has the following structure:

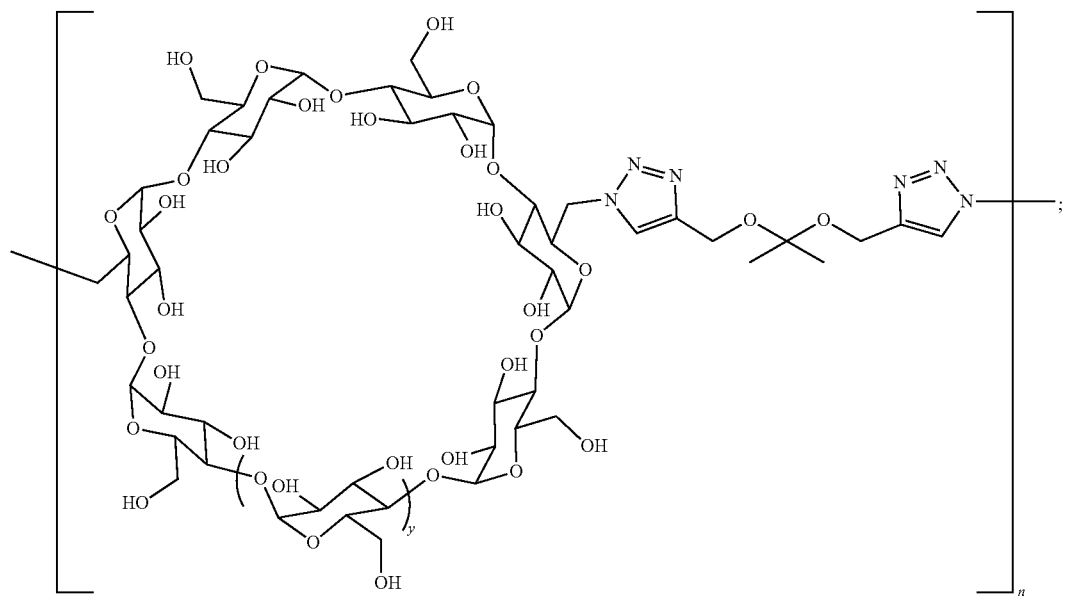

wherein y is 0, 1, or 2; and
n is from 4 to 1000.

In some embodiments, y is 0. In other embodiments, y is 1. In yet another embodiment, y is 2.

In another embodiment of the present method, n is from 10 to 100. In one embodiment, n is from 10 to 75. In one embodiment, n is from 15 to 65. In one embodiment, n is from 20 to 30. In one embodiment, n is from 50 to 65. In one embodiment, n is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 100. In one specific embodiment, n is about 17. In another specific embodiment n is about 25.

In one embodiment, the polymers of the present methods have a polydispersity index of from about 1 to about 1.5.

The present disclosure further relates to a method for managing or treating lipid storage disorders/lipidoses (e.g., glomerular diseases) in a subject having or suspected of having said disorder, comprising administering a therapeutically effective amount of the polymers of cyclodextrin conjugates to the subject. In an embodiment, the present disclosure provides a method for managing or treating lipid storage disorders in a subject having or suspected of having said disorder, the method comprising administering therapeutically effective amount a compound of the present disclosure, including but not limited to, polymers of cyclodextrin conjugates (pBCDK polymer) comprising repeating units of cyclodextrin moiety attached through a triazole-ketal-triazole linker, or a composition/formulation thereof.

Figure 18:
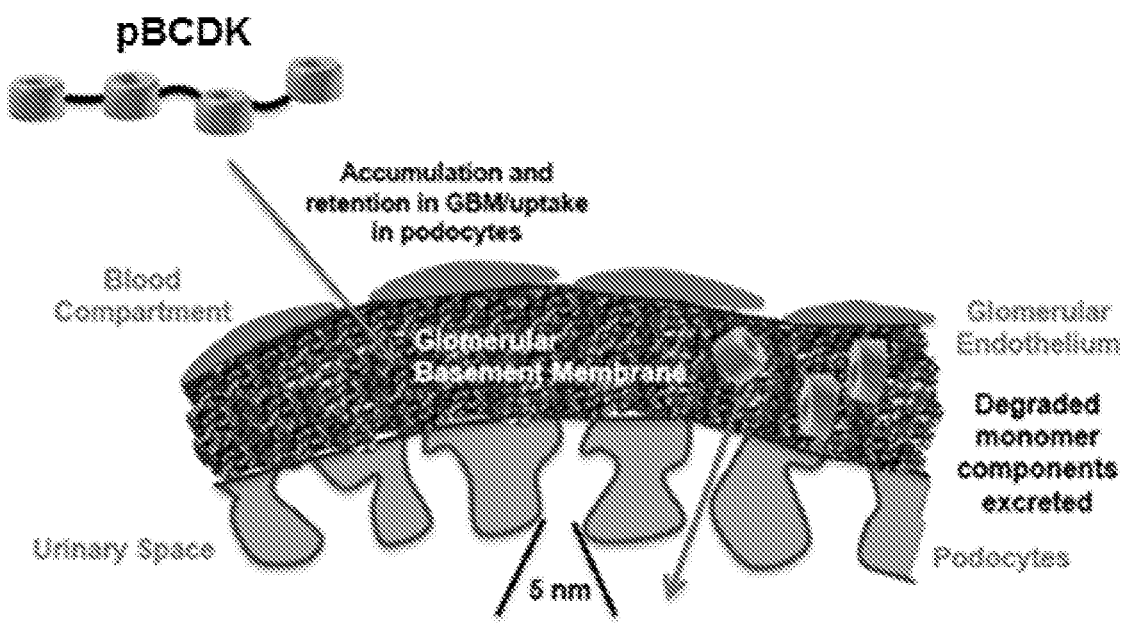
FIG. 18 is a schematic representation showing the action of cyclodextrin polymers of the present disclosure leading to the regulation/removal of over-accumulated cholesterol that protects podocytes from damage.

The polymers of the present invention are circulating, biocompatible, and can substantially increase cholesterol removal from cells lacking in the production enzymes needed to metabolize lipids or the production of enzymes lacking proper function (See FIG. 18 for a schematic representation. Further, the said polymers can deliver multiple copies/units of cyclodextrin or its derivatives to the lysosomes of cells.

In an embodiment of the present disclosure, the lipid storage disorder is a lysosomal lipid storage disorder. In another embodiment, the lysosomal lipid storage disorder is selected from the group consisting of sphingolipidoses, Wolman disease and a combination thereof. In yet another embodiment, the sphingolipidoses are selected from the group consisting of Niemann-Pick type C (NPC), Fabry disease, Krabbe disease, Gaucher disease, Tay-Sachs disease, Metachromatic leukodystrophy, Familial Hypercholesterolemia, Atherosclerosis, multiple sulfatase deficiency, Farber disease, and any combination thereof. In further embodiments of the present disclosure, the lipid storage disorder is a kidney disease, including glomerular diseases.

The present invention is based, in part, on the inventor's recognition that clinical and experimental studies have associated renal accumulation of cholesterol with the development of glomerulosclerosis (Merscher-Gomez et al., 2013 "Cyclodextrin Protects Podocytes in Diabetic Kidney Disease." Diabetes 62:3817-3827). The inventors further recognized that kidneys from diabetic rats have been shown to accumulate cholesterol. Excessive accumulation of cholesterol may be deleterious to cell function though several mechanisms including a modulation of cellular actin cytoskeleton, a modulation of the response of podocytes to several circulating factors (insulin, IGFs, VEGF, any growth factor, apolipoproteins, adipokines, endocrine hormones), a modulation of locally produced inflammatory cytokines, chemokines and their receptors, integrins, a modulation of the immune response (such as the one mediated through TLRs and co-stimulatory molecules as B7-1-CD80), or a modulation of pro- and anti-apoptotic cell death pathways.

Thus, in some embodiments, the present disclosure teaches methods of treating or managing glomerular diseases, including Focal Segmental Glomerulosclerosis, Alport Syndrome, Diabetic Kidney Disease, Minimal Change Kidney Disease, and Minimal Change Nephropathy, said method comprising administering a therapeutically effective amount of the polymers of cyclodextrin conjugates to the subject. In some embodiments the present disclosure teaches methods of administering cyclodextrin polymers to a patient having, or exhibiting one or more of the symptoms of Focal Segmental Glomerulosclerosis, Alport Syndrome, Diabetic Kidney Disease, Minimal Change Kidney Disease, and Minimal Change Nephropathy.

Kidney Glomerular Diseases

In one embodiment of the present disclosure, a method of treating kidney-associated diseases, comprising administering to a subject in need thereof a compound of the present disclosure, e.g., polymers comprising conjugates of cyclodextrins.

In some embodiments, the present disclosure teaches methods of treating glomerular diseases. Glomeruli are clusters of looping blood vessels within the kidney that clean and filter an animal's blood. In some embodiments, Glomerular diseases are those in which the glomeruli are no longer fulfilling this function. Damage to the glomeruli affects the kidney's ability to filter fluids and wastes properly. This leads to blood (hematuria) and/or protein (proteinuria) in the urine. Glomerular diseases are often associated with the signs and symptoms of nephrotic syndrome and predispose to acute renal failure, or progressive chronic kidney disease culminating in end-stage renal disease with dialysis or kidney transplantation.

In some embodiments, glomerular diseases are characterized by the presence of one or more of the following symptoms, including but not limited to: podocytopenia (decreased podocytopenia), podocyte insulin resistance, susceptibility to apoptosis, albuminuria (presence of protein in the urine), hematuria (presence of blood in the urine), reduced glomerular filtration rate (inefficient filtering of wastes from the blood), hypoproteinemia (low blood protein), and edema (swelling in parts of the body).

Glomerular diseases include many conditions with a variety of differing causes that can broadly categorized into two major categories namely, glomerulonephritis (inflammation of the tissue in the kidney that serve as a filter) and glomerulosclerosis (hardening or scarring of the blood vessels within the kidney). Illustrative glomerular diseases of the present disclosure are described below.

Diabetic Kidney Disease

In some embodiments, the present disclosure teaches methods of treating Diabetic Kidney Disease (DKD). DKD, one of the leading causes of kidney failure in the U.S., is a form of glomerular disease which is considered to be both a systemic disease, since diabetes itself is a systemic disease, and also a sclerotic disease.

Diabetic kidney disease a chronic kidney disease caused by or associated with diabetes. Symptoms of diabetic kidney disease include the occurrence of microalbuminuria or macroalbuminuria, or the progressive decline of GFR in a normoalbuminuric individual with any form of diabetes.

The main treatment, once proteinuria is established, is ACE inhibitor medications, which usually reduce proteinuria levels and slow the progression of diabetic nephropathy. Other issues that are important in the management of this condition include control of high blood pressure and blood sugar levels, as well as the reduction of dietary salt intake.

Focal Segmental Glomerulosclerosis

In some embodiments, the present disclosure provides methods of treating Focal segmental glomerulosclerosis (FSGS). FSGS is the most common primary glomerular disease leading to end-stage kidney disease (ESKD) due to glomerulonephritis in the US, particularly in children and young adults. Approximately 2000 individuals reach ESKD each year. The estimated life-time risk for FSGS is 0.17% in European Americans and 0.72% in African Americans (Kitiyakara C. et al. 2004 Twenty-one-year trend in ESRD due to focal segmental glomerulosclerosis in the United States. Am J Kidney Dis 44, 815-25). Susceptibility to FSGS in African Americans is associated with genetic variants of the APOL1 gene (G1 and G2) (Genovese G, Friedman D J, Ross M D, et al. 2010 Association of trypanolytic ApoL1 variants with kidney disease in African Americans. Science 329, 841-5). Thus in other embodiments, the present disclosure provides methods of treating FSGS associated with genetic variants of APOL1 genes, G1 and G2.

FSGS is a glomerular scarring disease characterized by an effacement of the podocyte foot when kidney biopsies are analyzed. Furthermore, when urine samples from patients suffering FSGS are analyzed, it is observed that massive urine protein is lost, which progresses, at the end, to a renal failure.

The pathogenesis of FSGS is associated with podocyte injury ultimately leading to glomerulosclerosis and end-stage kidney disease (see Kim Y.H., et al. 2001 Podocyte depletion and glomerulosclerosis have a direct relationship in the PAN-treated rat. Kidney Int 60, 957-968; Pagtalunan M. E., et al. 1997 Podocyte loss and progressive glomerular injury in type II diabetes. The Journal of clinical investigation 99, 342-348; Meyer T. W., et al. 1999 Podocyte number predicts long-term urinary albumin excretion in Pima Indians with Type II diabetes and microalbuminuria. Diabetologia 42, 1341-1344; White K. E., et al. 2002 Podocyte number in normotensive type 1 diabetic patients with albuminuria. Diabetes 51, 3083-3089; and Faul C. et al. 2007, Actin up: regulation of podocyte structure and function by components of the actin cytoskeleton. Trends Cell Biol 17, 428-437).

FSGS has also been associated with misregulation of lipid-related genes, hypothesized to result in an over accumulation of cholesterol. Recent studies suggest that cyclodextrin treatments could prevent podocyte injury through a reduction of cholesterol accumulation (Merscher-Gomez et al., 2013, "Cyclodextrin Protects Podocytes in Diabetic Kidney Disease" Diabetes 62:3817).

Alport Syndrome

In some embodiments, the present disclosure teaches methods of treating Alport syndrome. Alport Syndrome is a genetic condition characterized by kidney disease, hearing loss, and eye abnormalities, and occurs in approximately 1 in 50,000 newborns, accounting for about 2% of all end stage renal disease.

In other embodiments, the present disclosure provides methods of treating Alport Syndrome caused by mutations in the COL4A3, COL4A4, and COL4A5 genes. These genes each provide instructions for making one component of a protein called type IV collagen. This protein plays an important role in the kidneys glomeruli.Gradual scarring of the kidneys occurs, eventually leading to progressive loss of kidney function and end-stage renal disease in many people with Alport Syndrome.

Early and accurate diagnosis is important for early intervention in Alport Syndrome. The diagnostic approach in subjects with hematuria is based on careful evaluation of clinical features and family history, supplemented by tissue biopsy and molecular genetic analysis. Hematuria is present in Alport Syndrome long before hearing loss and ocular abnormalities are detectable. Therefore, while the presence of characteristic sensorineural deafness or ocular changes in a subject with hematuria increases suspicion for Alport Syndrome, normal hearing and eye examinations do not serve to rule out Alport Syndrome. A suspected diagnosis of Alport Syndrome can be confirmed by biopsy of the kidney or skin. Complete evaluation of kidney biopsy material requires light, immunofluorescence, and electron microscopy.

Kidney transplantation is usually offered to patients with Alport Syndrome who develop end-stage renal disease (ESRD). Recurrent disease does not occur in the transplanted kidney, and the allograft survival rate in these patients is similar to that in patients with other renal diseases. However, anti-glomerular basement membrane (anti-GBM) nephritis develops in a small percentage of transplant patients with Alport Syndrome.

Recent studies have linked Alport syndrome with the accumulation of lipid droplets in the kidney cortex of affected animals (Morales et al., 2015 "Cyclodextrin Improves Renal Function in Experimental Alport Syndrome" Poster Presentation Variant Pharma, available from http://content.stockpr.com/variantpharma/files/pages/pipeline/var-200-presentationspublications/ASN+Alport+2015+New.pdf).

Without wishing to be bound to any theory, the cyclodextrin when released from the polymers of the present invention is capable of complexing with the overexpressed cholesterol or other overexpressed lipids and effluxing it out of the lysosome and thereby significantly reducing the cholesterol content in cells, thereby managing/treating lipid storage disorders (Lopez C A, de Vries A H, Marrink S J. Molecular mechanism of cyclodextrin mediated cholesterol extraction. PLOS Comput Biol 2011;7:e1002020). Alternatively, without being released from the pBCDK, the cyclodextrin moieties could bind cholesterol or other overexpressed lipids in their available cavities, followed by the aforementioned effluxing step as a means of reducing lipid content in cells.

The present disclosure thus also relates to a method of removing lipid from cells of a subject (i.e. reducing lipid content of said cells), said method comprising step of administering a therapeutically effective amount of the polymers of cyclodextrin conjugates to the subject.

In some embodiments, said removing cholesterol is a complete removing of cholesterol from cells. In still another embodiment, said removing is a partial removing. Partial removal can be about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% of the cholesterol in cells, inclusive of all values therebetween.

In an embodiment, the lipid includes but is not limited to cholesterol. In an exemplary embodiment, a method of removing cholesterol from cells of a subject is provided, said method comprising step of administering therapeutically effective amount of a compound of the present disclosure, including but not limited to, polymers of cyclodextrin conjugates (pBCDK polymer) comprising repeating units of cyclodextrin moiety attached through triazole-ketal-triazole linker, or a composition/formulation thereof In an embodiment of the present disclosure, the subject is a mammal, including but not limited to, human.

Without wishing to be bound to any theory, upon administration of the present pBCDK polymer or a composition/formulation thereof, said polymer can accumulate in the different affected organs in the body such as liver, kidney, lungs, spleen and brain. Once in the organs and upon cellular internalization, the polymers can enter the cells and degrade to afford free cyclodextrins, followed by the cyclodextrins complexing with the excess cholesterol in the lysosomes. This removal of cholesterol then reduces the diseased state of the cells/organs hence affording the therapeutic effect.

As used in the present disclosure, the expression "management" or "managing" refers to preventing a disease or disorder or condition from occurring in a subject, decreasing the risk of death due to a disease or disorder or condition, delaying the onset of a disease or disorder or condition, inhibiting the progression of a disease or disorder or condition, partial or complete cure of a disease or disorder or condition and/or adverse effect attributable to the said disease or disorder or condition, obtaining a desired pharmacologic and/or physiologic effect (the effect may be prophylactic in terms of completely or partially preventing a disorder or disease or condition, or a symptom thereof and/or may be therapeutic in terms of a partial or complete cure for a disease or disorder or condition and/or adverse effect attributable to the disease or disorder), relieving a disease or disorder or condition (i.e., causing regression of the disease or disorder or condition).

Thus, the use of the term "management" in reference to the glomerular diseases of the present disclosure can refer, in some embodiments, to a reduction of severity of one or more of the symptoms associated with said disease. For example, in some embodiments, a patient diagnosed with a glomerular disease may manage his or her disease through methods of the present disclosure to bring about a reduction in any one or more of the following symptoms: podocytopenia (decreased podocytopenia), podocyte insulin resistance, susceptibility to apoptosis, albuminuria (presence of protein in the urine), hematuria (presence of blood in the urine), reduced glomerular filtration rate (inefficient filtering of wastes from the blood), hypoproteinemia (low blood protein), and edema (swelling in parts of the body).

In some embodiments of the above methods, the pBCDK polymer removes overexpressed lipid in kidney cells. In some embodiments, the lipid includes but is not limited to cholesterol.

The present invention further relates to the use of polymers of cyclodextrin conjugates or compositions/formulations thereof in management or treatment of lipid storage disorders. In one embodiment, use of pBCDK polymer or compositions/formulations comprising the same for management of lipid storage disorders is provided.

In an embodiment, the lipid storage disorder is lysosomal lipid storage disorder. In another embodiment, the lysosomal lipid storage disorder is selected from the group consisting of sphingolipidoses, Wolman disease and a combination thereof. In yet another embodiment, the sphingolipidoses are selected from the group consisting of Niemann-Pick type C (NPC), Fabry disease, Krabbe disease, Gaucher disease, Tay-Sachs disease, Metachromatic leukodystrophy, Familial Hypercholesterolemia, Atherosclerosis, multiple sulfatase deficiency, Farber disease, renal disorders that are a cholesterol homeostasis such as Focal Segmental Glomerulosclerosis, Alport Syndrome, Diabetic Kidney, and combinations thereof.

In one embodiment, the polymer of the present disclosure has an elimination half-life of from about 6 hours to about 24 hours.

In one embodiment, the bioavailability of a therapeutically active agent administered with a polymer of the present disclosure is improved.

Pharmaceutical Compositions

In an exemplary embodiment, the present disclosure provides pBCDK polymer or compositions/formulations thereof for use in managing or treating glomerular diseases.

The present disclosure also provides a pharmaceutical composition or formulation comprising therapeutically effective amount of a polymers described herein, optionally along with excipient(s). In one embodiment of the present disclosure, a pharmaceutical composition is provided comprising a pharmaceutically acceptable carrier or a pharmaceutical excipient and a polymer of the present disclosure, e.g., polymers of cyclodextrin conjugates (pBCDKs). In another embodiment, the pharmaceutical composition disclosed herein further comprises one or more additional therapeutically active agents. In another embodiment, the pharmaceutical composition disclosed herein further comprises one or more additional therapeutically active agents and one or more pharmaceutically acceptable carriers and/or excipients. In related embodiments, the one or more additional therapeutically active agents are selected from the group consisting of angiotensin-converting-enzyme (ACE) inhibitors and angiotensin receptor blockers (ARBs). In various embodiments, the one or more additional therapeutically active agents are selected from the group consisting of angiotensin-converting-enzyme (ACE) inhibitors. In specific embodiments, the one or more ACE inhibitors are selected from the group consisting of captopril, zofenopril. enalapril, ramipril, quinapril, perindopril, lisinopril, benazepril, imidapril, trandolapril, cilazapril, and fosinopril. In various other embodiments, the one or more additional therapeutically active agents are selected from the group consisting of angiotensin receptor blockers (ARBs). In specific embodiments, the one or more ARBs are selected from the group consisting of azilsartan, candesartan, eprosartan, irbesartan, losartan, olmesartan, telmisartan, and valsartan.

In an embodiment of the present disclosure, the excipient is selected from, but not limited to, granulating agent, binding agent, lubricating agent, disintegrating agent, sweetening agent, glidant, anti-adherent, anti-static agent, surfactant, anti-oxidant, gum, coating agent, coloring agent, flavouring agent, coating agent, plasticizer, preservative, suspending agent, emulsifying agent, plant cellulosic material, spheronization agents and combinations thereof.

In a further embodiment of the present disclosure, a pharmaceutical composition comprising one or more polymers of the present disclosure, e.g., polymers comprising conjugates of cyclodextrins, and a pharmaceutically acceptable excipient or adjuvant is provided. The pharmaceutically acceptable excipients and adjuvants are added to the composition or formulation for a variety of purposes. In another embodiment, a pharmaceutical composition comprising one or more polymers of the present disclosure, e.g., polymers comprising conjugates of cyclodextrins, further comprises a pharmaceutically acceptable carrier. In one embodiment, a pharmaceutically acceptable carrier includes a pharmaceutically acceptable excipient, binder, and/or diluent. In one embodiment, suitable pharmaceutically acceptable excipients include, but are not limited to, water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, the pharmaceutical compositions of the present disclosure may additionally contain other adjunct components conventionally found in pharmaceutical compositions, at their art-established usage levels. Thus, for example, the pharmaceutical compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions described herein. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

Cyclodextrin Polymer Dosage and Administration

In particular, a pharmaceutical composition or formulation comprising about 4 mg/kg body weight (b.w.) to 4000 mg/kg b.w. of the patient of pBCDK polymer, optionally along with excipient(s) is provided.

In an embodiment, a pharmaceutical composition or formulation comprising about 4 mg/kg b.w. to 120 mg/kg b.w. of the patient of pBCDK polymer, optionally along with excipient(s) is provided.

In another embodiment, a pharmaceutical composition or formulation comprising 4 mg/kg b.w.to 400 mg/kg b.w. of the patient of pBCDK polymer, optionally along with excipient(s) is provided.

In yet another embodiment, a pharmaceutical composition or formulation comprising 100 mg/kg b.w. to 1000 mg/kg b.w. of the patient of pBCDK polymer, optionally along with excipient(s) is provided.

In still another embodiment, a pharmaceutical composition or formulation comprising 200 mg/kg b.w. to 2000 mg/kg b.w. of the patient of pBCDK polymer, optionally along with excipient(s) is provided.

In still another embodiment, a pharmaceutical composition or formulation comprising 300 mg/kg b.w. to 3000 mg/kg b.w. of the patient of pBCDK polymer, optionally along with excipient(s) is provided.

In certain embodiments, the pharmaceutical formulation comprises the present polymer in an amount of from about 1 mg/kg b.w. to about 10 g/kg b.w. In some embodiments, the pharmaceutical formulation comprises the present polymer in an amount of about 2 mg/kg b.w. In some embodiments, the pharmaceutical formulation comprises the present polymer in an amount of about 3 mg/kg b.w. In some embodiments, the pharmaceutical formulation comprises the present polymer in an amount of about 4 mg/kg b.w. In some embodiments, the pharmaceutical formulation comprises the present polymer in an amount of about 5 mg/kg b.w. In some embodiments, the pharmaceutical formulation comprises the present polymer in an amount of about 6 mg/kg b.w. In some embodiments, the pharmaceutical formulation comprises the present polymer in an amount of about 7 mg/kg b.w. In some embodiments, the pharmaceutical formulation comprises the present polymer in an amount of about 8 mg/kg b.w. In some embodiments, the pharmaceutical formulation comprises the present polymer in an amount of about 9 mg/kg b.w. In some embodiments, the pharmaceutical formulation comprises the present polymer in an amount of about 10 mg/kg b.w. In some embodiments, the pharmaceutical formulation comprises the present polymer in an amount of about 20 mg/kg b.w. In some embodiments, the pharmaceutical formulation comprises the present polymer in an amount of about 30 mg/kg b.w. In some embodiments, the pharmaceutical formulation comprises the present polymer in an amount of about 40 mg/kg b.w. In some embodiments, the pharmaceutical formulation comprises the present polymer in an amount of about 50 mg/kg b.w. In some embodiments, the pharmaceutical formulation comprises the present polymer in an amount of about 60 mg/kg b.w. In some embodiments, the pharmaceutical formulation comprises the present polymer in an amount of about 70 mg/kg b.w. In some embodiments, the pharmaceutical formulation comprises the present polymer in an amount of about 80 mg/kg b.w. In some embodiments, the pharmaceutical formulation comprises the present polymer in an amount of about 90 mg/kg b.w. In some embodiments, the pharmaceutical formulation comprises the present polymer in an amount of about 100 mg/kg b.w. In some embodiments, the pharmaceutical formulation comprises the present polymer in an amount of about 200 mg/kg b.w. In some embodiments, the pharmaceutical formulation comprises the present polymer in an amount of about 300 mg/kg b.w. In some embodiments, the pharmaceutical formulation comprises the present polymer in an amount of about 400 mg/kg b.w. In some embodiments, the pharmaceutical formulation comprises the present polymer in an amount of about 500 mg/kg b.w. In some embodiments, the pharmaceutical formulation comprises the present polymer in an amount of about 600 mg/kg b.w. In some embodiments, the pharmaceutical formulation comprises the present polymer in an amount of about 700 mg/kg b.w. In some embodiments, the pharmaceutical formulation comprises the present polymer in an amount of about 800 mg/kg b.w. In some embodiments, the pharmaceutical formulation comprises the present polymer in an amount of about 900 mg/kg b.w. In some embodiments, the pharmaceutical formulation comprises the present polymer in an amount of about 1000 mg/kg b.w. In some embodiments, the pharmaceutical formulation comprises the present polymer in an amount of about 2000 mg/kg b.w. In some embodiments, the pharmaceutical formulation comprises the present polymer in an amount of about 3000 mg/kg b.w.

In an embodiment of the present disclosure, the patient is a mammal, including but not limited to, a human.

In another aspect of the present disclosure, the polymer of the present disclosure or the pharmaceutical composition/formulation comprising the same is administered by mode selected from the group consisting of intravenous, subcutaneous, transdermal, intrathecal, intranasal, intracisternal, oral and any other compatible mode and combinations thereof In one embodiment, the pBCDK polymer of the present disclosure or the pharmaceutical composition/formulation comprising the same is administered subcutaneously, intranasally or a combination thereof In an exemplary embodiment, the pBCDK polymer of the present disclosure or the pharmaceutical composition/formulation comprising the same is administered subcutaneously.

In another exemplary embodiment, the pBCDK polymer of the present disclosure or the pharmaceutical composition/formulation comprising the same is administered intranasally.

In yet another exemplary embodiment, the pBCDK polymer of the present disclosure or the pharmaceutical composition/formulation comprising the same is administered by a combination of subcutaneous and intranasal administration.

The polymers disclosed herein can be formulated in accordance with the routine procedures adapted for desired administration route. Accordingly, the polymers disclosed herein can take such forms as suspensions, solutions or emulsions in oily or aqueous vehicles, and can contain formulatory agents such as suspending, stabilizing and/or dispersing agents. The polymers disclosed herein can also be formulated as a preparation for implantation or injection. Thus, for example, the polymers can be formulated with suitable polymeric or hydrophobic materials (e.g., as an emulsion in an acceptable oil) or ion exchange resins, or as sparingly soluble derivatives (e.g., as a sparingly soluble salt). Alternatively, the active ingredient can be in powder form for constitution with a suitable vehicle, e.g., sterile pyrogen-free water, before use. Suitable formulations for each of these methods of administration can be found, for example, in Remington: The Science and Practice of Pharmacy, A. Gennaro, ed., 20th edition, Lippincott, Williams & Wilkins, Philadelphia, Pa.

In another embodiment of the present disclosure, the pharmaceutical composition/formulation is formulated into forms selected from, but not limited to, solution, aqueous suspension, capsule, tablet, injection, cream, gel, ointment, lotion, emulsion, foam, troche, lozenge, oily suspension, patch, dentifrice, spray, drops, dispersible powder or granule, syrup, elixir, food stuff, and any combination of forms thereof.

The polymer technology approach of the present disclosure provides increased retention time of cyclodextrin in the body thereby improving the pharmacokinetic and biodistribution profile and hence enabling prolonged therapeutic action. This can be attributed to the reduced rate of renal clearance due to its large size. Consequently, the doses required to maintain therapeutic concentrations are significantly reduced in view of the prolonged circulation time in the body. This in turn allows less frequent administration which increases patient compliance significantly.

In an embodiment of the above methods, the subject is a mammal including but not limiting to human.

Formulation and Manufacturing

In certain embodiments, a pharmaceutical composition of the present disclosure is prepared using known techniques, including, but not limited to mixing, dissolving, granulating, dragee-making, levigating, emulsifying, encapsulating, entrapping or tableting processes.

In one embodiment, the present disclosure provides a pharmaceutical composition comprising a polymer of the present disclosure, e.g., polymers comprising conjugates of cyclodextrins, as disclosed herein, combined with a pharmaceutically acceptable carrier. In one embodiment, suitable pharmaceutically acceptable carriers include, but are not limited to, inert solid fillers or diluents and sterile aqueous or organic solutions. Pharmaceutically acceptable carriers are well known to those skilled in the art and include, but are not limited to, from about 0.01 to about 0.1 M and preferably 0.05M phosphate buffer or 0.8% saline. Such pharmaceutically acceptable carriers can be aqueous or non-aqueous solutions, suspensions and emulsions. Examples of non-aqueous solvents suitable for use in the present application include, but are not limited to, propylene glycol, polyethylene glycol, vegetable oils such as olive oil, and injectable organic esters such as ethyl oleate.

Aqueous carriers suitable for use in the present application include, but are not limited to, water, ethanol, alcoholic/aqueous solutions, glycerol, emulsions or suspensions, including saline and buffered media. Oral carriers can be elixirs, syrups, capsules, tablets and the like.

Liquid carriers suitable for use in the present application can be used in preparing solutions, suspensions, emulsions, syrups, elixirs and pressurized polymers. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid carriers suitable for use in the present application include, but are not limited to, water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also include an oily ester such as ethyl oleate and isopropyl myristate. Sterile liquid carriers are useful in sterile liquid form comprising polymers for parenteral administration. The liquid carrier for pressurized polymers disclosed herein can be halogenated hydrocarbon or other pharmaceutically acceptable propellant.

Solid carriers suitable for use in the present application include, but are not limited to, inert substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets preferably contain up to 99% of the active compound. Suitable solid carriers include, for example, calcium phosphate, magnesium stearate, talc, sugars, lactose, dextrin, starch, gelatin, cellulose, polyvinylpyrrolidone, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

Parenteral carriers suitable for use in the present application include, but are not limited to, sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like.

Carriers suitable for use in the present application can be mixed as needed with disintegrants, diluents, granulating agents, lubricants, binders and the like using conventional techniques known in the art. The carriers can also be sterilized using methods that do not deleteriously react with the polymers, as is generally known in the art.

Diluents may be added to the formulations of the present invention. Diluents increase the bulk of a solid pharmaceutical composition and/or combination, and may make a pharmaceutical dosage form containing the composition and/or combination easier for the patient and care giver to handle. Diluents for solid compositions and/or combinations include, for example, microcrystalline cellulose (e.g., AVICEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT(r)), potassium chloride, powdered cellulose, sodium chloride, sorbitol, and talc.

Additional embodiments relate to the pharmaceutical formulations wherein the formulation is selected from the group consisting of a solid, powder, liquid and a gel. In certain embodiments, a pharmaceutical composition of the present invention is a solid (e.g., a powder, tablet, a capsule, granulates, and/or aggregates). In certain of such embodiments, a solid pharmaceutical composition comprising one or more ingredients known in the art, including, but not limited to, starches, sugars, diluents, granulating agents, lubricants, binders, and disintegrating agents.

Solid pharmaceutical compositions that are compacted into a dosage form, such as a tablet, may include excipients whose functions include helping to bind the active ingredient and other excipients together after compression. Binders for solid pharmaceutical compositions and/or combinations include acacia, alginic acid, carbomer (e.g., carbopol), carboxymethylcellulose sodium, dextrin, ethyl cellulose, gelatin, guar gum, gum tragacanth, hydrogenated vegetable oil, hydroxyethyl cellulose, hydroxypropyl cellulose (e.g., KLUCEL), hydroxypropyl methyl cellulose (e.g., METHOCEL), liquid glucose, magnesium aluminum silicate, maltodextrin, methylcellulose, polymethacrylates, povidone (e.g., KOLLIDON, PLASDONE), pregelatinized starch, sodium alginate, and starch.

The dissolution rate of a compacted solid pharmaceutical composition in the patient's stomach may be increased by the addition of a disintegrant to the composition and/or combination. Disintegrants include alginic acid, carboxymethylcellulose calcium, carboxymethylcellulose sodium (e.g., AC-DI-SOL and PRIMELLOSE), colloidal silicon dioxide, croscarmellose sodium, crospovidone (e.g., KOLLIDON and POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB), potato starch, and starch.

Glidants can be added to improve the flowability of a non-compacted solid composition and/or combination and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition and/or combination to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition and/or combination of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

Liquid pharmaceutical compositions can be prepared using polymers of the present disclosure, e.g., polymers comprising conjugates of cyclodextrins, and any other solid excipients where the components are dissolved or suspended in a liquid carrier such as water, vegetable oil, alcohol, polyethylene glycol, propylene glycol, or glycerin.

For example, formulations for parenteral administration can contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers can be useful excipients to control the release of active compounds. Other potentially useful parenteral delivery systems include ethylene-vinyl acetate copolymer particles, osmotic pumps, implantable infusion systems, and liposomes. Formulations for inhalation administration contain as excipients, for example, lactose, or can be aqueous solutions containing, for example, polyoxyethylene-9-auryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or citric acid for vaginal administration.

Liquid pharmaceutical compositions can contain emulsifying agents to disperse uniformly throughout the composition and/or combination an active ingredient or other excipient that is not soluble in the liquid carrier. Emulsifying agents that may be useful in liquid compositions and/or combinations of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as aspartame, lactose, sorbitol, saccharin, sodium saccharin, sucrose, aspartame, fructose, mannitol, and invert sugar may be added to improve the taste.

Preservatives and chelating agents such as alcohol, sodium benzoate, butylated hydroxyl toluene, butylated hydroxyanisole, and ethylenediamine tetraacetic acid may be added at levels safe for ingestion to improve storage stability.

A liquid composition can also contain a buffer such as gluconic acid, lactic acid, citric acid or acetic acid, sodium gluconate, sodium lactate, sodium citrate, or sodium acetate. Selection of excipients and the amounts used may be readily determined by the formulation scientist based upon experience and consideration of standard procedures and reference works in the field.

In one embodiment, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Formulations for intravenous administration can comprise solutions in sterile isotonic aqueous buffer. Where necessary, the formulations can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the polymer is to be administered by infusion, it can be dispensed in a formulation with an infusion bottle containing sterile pharmaceutical grade water, saline or dextrose/water. Where the polymer is administered by injection, an ampule of sterile water for injection or saline can be provided so that the ingredients can be mixed prior to administration.

Suitable formulations further include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethyl sulfoxide are used.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80 and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80; the fraction size of polyethylene glycol may be varied; other biocompatible polymers may replace polyethylene glycol, e.g., polyvinylpyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

Appropriate pharmaceutical compositions of the present disclosure can be determined according to any clinically-acceptable route of administration of the composition to the subject. The manner in which the composition is administered is dependent, in part, upon the cause and/or location. One skilled in the art will recognize the advantages of certain routes of administration. The method includes administering an effective amount of the agent or compound (or composition comprising the agent or compound) to achieve a desired biological response, e.g., an amount effective to alleviate, ameliorate, or prevent, in whole or in part, a symptom of a condition to be treated, e.g., oncology and neurology disorders. In various aspects, the route of administration is systemic, e.g., oral or by injection. The agents or polymer, or pharmaceutically acceptable salts or derivatives thereof, are administered orally, nasally, transdermally, pulmonary, inhalationally, buccally, sublingually, intraperintoneally, subcutaneously, intramuscularly, intravenously, rectally, intrapleurally, intrathecally, intraportally, and parenterally. Alternatively or in addition, the route of administration is local, e.g., topical, intra-tumor and peri-tumor. In some embodiments, the polymer is administered orally.

In certain embodiments, a pharmaceutical composition of the present disclosure is prepared for oral administration. In certain of such embodiments, a pharmaceutical composition is formulated by combining one or more agents and pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinylpyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In other embodiments the polymer of the present disclosure are administered by the intravenous route. In further embodiments, the parenteral administration may be provided in a bolus or by infusion.

In certain embodiments, a pharmaceutical composition is prepared for rectal administration, such as a suppository or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

The concentration of a disclosed polymer in a pharmaceutically acceptable mixture will vary depending on several factors, including the dosage of the polymer to be administered, the pharmacokinetic characteristics of the polymer(s) employed, and the route of administration.

The agent may be administered in a single dose or in repeat doses. The dosage regimen utilizing the polymers of the present invention is selected in accordance with a variety of factors including type, species, age, weight, sex and medical condition of the patient; the severity of the condition to be treated; the route of administration; the renal and hepatic function of the patient; and the particular polymer employed. Treatments may be administered daily or more frequently depending upon a number of factors, including the overall health of a patient, and the formulation and route of administration of the selected compound(s). An ordinarily skilled physician or veterinarian can readily determine and prescribe the effective amount of the polymer required to prevent, counter or arrest the progress of the condition.

The polymers or pharmaceutical compositions of the present disclosure may be manufactured and/or administered in single or multiple unit dose forms.

Representative Embodiments

The polymers of the present disclosure can be useful for treating a condition or a disease associated with abnormal lipid storage. In some embodiments, the present disclosure provides a method for treating a kidney glomerular disease, said method comprising administering to a subject in need thereof, an effective amount of a cyclodextrin polymer. having the following structure:

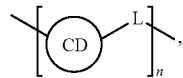

wherein
CD is a cyclodextrin moiety, or a derivative thereof;
L is a linker moiety; and
n is from 4 to 1000.

In some embodiments of the present method, the cyclodextrin moiety is selected from the group consisting of α-cyclodextrin, β-cyclodextrin, γ-cyclodextrin, derivatives thereof, and combinations thereof. In other embodiments of the present method, the cyclodextrin moiety is a derivative thereof selected from the group consisting of hydroxyalkyl-α-cyclodextrin, hydroxyalkyl-β-cyclodextrin, hydroxyalkyl-γ-cyclodextrin, derivatives thereof, a salt thereof, a solvate thereof, and combinations thereof.

In various other embodiments of the present method, the cyclodextrin moiety is selected from the group consisting of β-cyclodextrin, (2-hydroxypropyl)-β-cyclodextrin, derivatives thereof, a salt thereof, a solvate thereof, and combinations thereof. In related embodiments of the present method, the cyclodextrin moiety is β-cyclodextrin or (2-hydroxypropyl)-β-cyclodextrin.

In still other embodiments of the present method, the alkyl of the hydroxyalkyl cyclodextrin is selected from the group consisting of $C_1$-$C_{10}$ linear alkyl, $C_1$-$C_{10}$ branched alkyl, and $C_1$-$C_{10}$ cycloalkyl, each further comprising one or more optional substituents. In related embodiments of the present method, the one or more optional substituents are selected from methyl, ethyl and butyl.

In various embodiments of the present method, the polymers of the present disclosure comprise a linker L having the following structure:

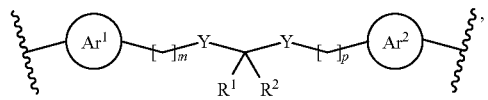

wherein $Ar^1$ and $Ar^2$ are each independently a 5- or 6-membered heteroaryl comprising 1, 2, 3 or 4 heteroatoms individually selected from N, O, and S, and wherein $Ar^1$ and $Ar^2$ are optionally substituted with 1 to 3 $R^3$ groups. In various embodiments, $Ar^1$ and $Ar^2$ are each triazole. In other embodiments, $Ar^1$ and $Ar^2$ are the same. In certain embodiments, $R^1$ and $R^2$ are each independently $R^4$, $OR^4$, $SR^4$ or $R^1$ and $R^2$ taken together with the carbon atom to which they are attached form a double bonded O, S, or $NR^4$. In some embodiments, $R^1$ and $R^2$ are each C1-C3 alkyl. In specific embodiments, $R^1$ and $R^2$ are each methyl. In various embodiments, $R^3$ is $C_1$-$C_3$ alkyl. In some embodiments, $R^3$ is selected from the group consisting of $C_1$-$C_3$ alkyl, $C_1$-$C_3$ alkyl sulfide, hydrazine, amine and halogen. In other embodiments, $R^4$ is H or a saturated or unsaturated $C_1$-$C_{10}$ linear alkyl, saturated or unsaturated $C_1$-$C_{10}$ branched alkyl, or saturated or unsaturated $C_1$-$C_{10}$ cycloalkyl, each of which is optionally substituted.

In various embodiments of the present method, Y is independently O, S, or $NR^4$. In other embodiments of the present disclosure, Y is O.

In other embodiments of the present method, m and p are each independently an integer from 1 to 10. In specific embodiments, m and p are both 1.

In various other embodiments of the present method, L comprises the following structure:

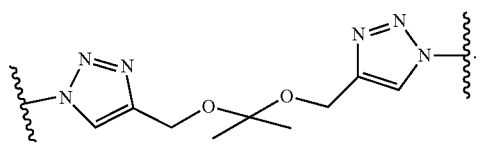 [SMILES: *n1cc(COC(C)(C)OCc2cn(*)nn2)nn1]

In certain embodiments, the present disclosure provides a method for treating a kidney glomerular disease, said method comprising administering to a subject in need thereof, an effective amount of a cyclodextrin polymer having the following structure:

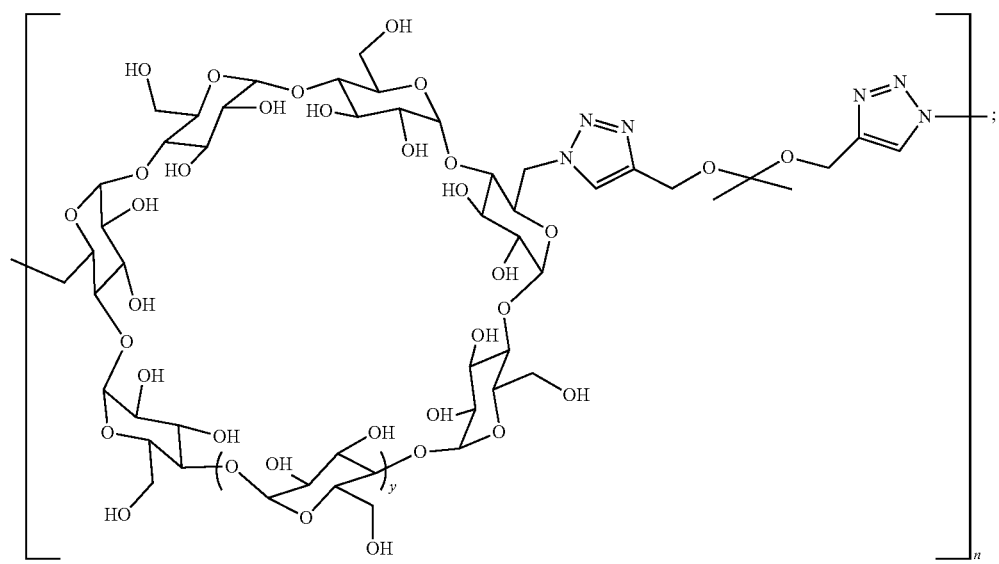

wherein n is from 4 to 1000.

In some embodiments of the present method, n is from 10 to 100. In other embodiments, n is from 10 to 75. In various embodiments, n is from 15 to 65. In some other embodiments, n is from 20 to 30. In related embodiments, n is from 50 to 65. In certain other embodiments, n is about 17. In other certain embodiments, n is about 25.

In various embodiments of the present method, the method for treating a kidney glomerular disease further comprises a pharmaceutically acceptable excipient. In other embodiments of the present method, the method further comprises one or more additional therapeutically active agents. In certain embodiments, the method comprises one or more angiotensin-converting enzyme inhibitors. In specific embodiments, the method comprises one or more angiotensin-converting enzyme inhibitors selected from the group consisting of captopril, zofenopril. enalapril, ramipril, quinapril, perindopril, lisinopril, benazepril, imidapril, trandolapril, cilazapril, and fosinopril. In other certain embodiments, the method comprises one or more angiotensin receptor blockers. In specific embodiments, method comprises one or more angiotensin receptor blockers selected from the group consisting of azilsartan, candesartan, eprosartan, irbesartan, losartan, olmesartan, telmisartan, sparsentan, and valsartan.

In other various embodiments, the methods are useful in treating kidney glomerular disease, wherein the kidney glomerular disease is glomerulonephritis or glomerulosclerosis. In various embodiments, the present disclosure provides methods of treating kidney glomerular disease, wherein the kidney glomerular disease is selected from the group consisting of: Focal Segmental Glomerulosclerosis, Alport Syndrome, Diabetic Kidney Disease, Minimum Change Kidney Disease, and Minimum Change Nephropathy. In related embodiments of the present methods, the kidney glomerular disease includes podocyte affected diseases.

In some embodiments of the present methods, the mean blood urea nitrogen level in a subject afflicted with kidney glomerular disease after treatment is substantially similar to the level in a subject not afflicted with a kidney glomerular disease having normal kidney function.

In other embodiments of the present invention, the mean albumin to creatinine ratio in a subject afflicted with kidney glomerular disease after treatment is substantially similar to the ratio in a subject not afflicted with a kidney glomerular disease having normal kidney function.

In various embodiments of the present disclosure, the method is useful for reducing lipid content in a cell or plasma membrane of a cell in a patient suffering from a kidney glomerular disease, said method comprising administering to the patient in need thereof, an effective amount of the cyclodextrin polymer having the following structure:

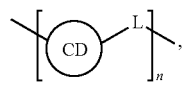

wherein
CD is a cyclodextrin moiety, or a derivative thereof;
L is a linker moiety; and
n is from 4 to 1000.

In some embodiments of the present method, the cyclodextrin polymer compound or compositions is administered by a route selected from intramuscular, intraperitoneal, intravenous (systemic), subcutaneous, transdermal, oral, rectal, inhalation, topical, and intranasal. In other embodiments, the cyclodextrin polymer is administered at a dose ranging from about 10 mg/kg/day or about 200 mg/kg/week.

Cyclodextrin Polymer Synthesis

The present disclosure also relates to a process of preparing polymers of cyclodextrin conjugates comprising repeating units of cyclodextrin moiety attached through a linker molecule. In the process for preparing polymers of cyclodextrin conjugates, the repeating units of cyclodextrins or its derivatives are attached via a linker molecules to afford pBCDK polymers.

In an embodiment of the present disclosure, a presentative process of preparing a pBCDK polymer comprises steps of:
1. reacting a cyclodextrin (CD) with a biphenyl-4,4'-disulfonyl halide derivative to obtain a biphenyl-4,4'-disulfonate capped CD;
2. reacting a biphenyl-4,4'-disulfonatecapped CD with sodium azide to obtain a diazide derivative of CD; and
3. carrying out a click reaction (1,3-dipolar cycloaddition reaction) between a diazide derivative of CD and

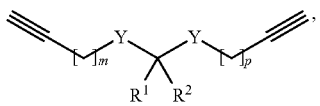

wherein
Y is O, S, or NR$^4$;
m and p is each independently an integer from 1 to 10;
R$^1$ and R$^2$ are each independently R$^4$, OR$^4$, SR$^4$ or R$^1$ and R$^2$ together form a double bonded O, S, or NR$^4$; and
R$^3$ is selected from C$_1$-C$_3$ alkyl, C$_1$-C$_3$ alkyl sulphide, hydrazone, amine, and halogen.
R$^4$ is H or a saturated or unsaturated C$_1$-C$_{10}$ linear alkyl, saturated or unsaturated C$_1$-C$_{10}$ branched alkyl, or saturated or unsaturated C$_1$-C$_{10}$ cycloalkyl, each of which are optionally substituted.

In another embodiment of the present disclosure, Y is O.
In some embodiments, m and p are each independently 1, 2, 3, 4, or 5. In other embodiments, m and p are both 1.
In one embodiment, R$^1$ and R$^2$ are each C1-C6 alkyl. In some embodiments, R$^1$ and R$^2$ are each C1-C3 alkyl. In one embodiment R$^1$ and R$^2$ are each selected form methyl, ethyl, propyl, and isopropyl. In one embodiment, wherein R$^1$ and R$^2$ are each methyl.

In other embodiments of the process for preparing pBCDK polymers, the disulfonate capped CD is prepared using a biphenyl-4,4'-disulfonyl halide selected from the group consisting of biphenyl-4,4'-disulfonyl chloride, biphenyl-4,4'-disulfonyl bromide, and biphenyl-4,4'-disulfonyl iodide. In a specific embodiment, the biphenyl-4,4'-disulfonyl halide is biphenyl-4,4'-disulfonyl chloride. In still other embodiments, the disulfonate capped CD is prepared using a 4,4'-trans-stilbenedisulfonyl halide selected from the group consisting of 4,4'-trans-stilbenedi sulfonyl chloride, 4,4'-trans-stilbenedisulfonyl bromide, and 4,4'-trans-stilbenedisulfonyl iodide. In another specific embodiment, the 4,4'-trans-stilbenedisulfonyl halide is 4,4'-trans-stilbenedisulfonyl chloride.

In an embodiment of the above process,

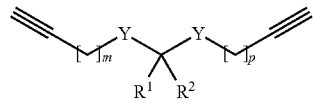

is obtained by reacting a ketone with trialkylsiloxy-1-alkyne in presence of trialkylsilyl triflate and organic solvent.

The process as described above for preparing pBCDK polymers is applicable to a number of different cyclodextrins and related molecules. In some embodiments, the cyclodextrin moiety or derivative thereof, used in the process of preparing polymers of the present invention is selected from α-cyclodextrin, β-cyclodextrin, γ-cyclodextrin, derivatives thereof, salts thereof, and combinations thereof. In other embodiments, the cyclodextrin moiety or a derivative thereof used in the process of preparing polymers of the present invention is a hydroxyalkyl-α-cyclodextrin, hydroxyalkyl-β-cyclodextrin, hydroxyalkyl-γ-cyclodextrin, derivatives thereof, salts thereof, and combinations thereof. In one embodiment, the alkyl in hydroxyalkyl-α-cyclodextrin, hydroxyalkyl-β-cyclodextrin, hydroxyalkyl-γ-cyclodextrin, derivatives thereof, a salt thereof, a solvate thereof, is selected from C$_1$-C$_{10}$ linear alkyl, C$_1$-C$_{10}$ branched alkyl and C$_1$-C$_{10}$ cycloalkyl, each optionally substituted. In some embodiments, the optional substituent for alkyl is selected from methyl, ethyl and butyl. In still other embodiments of the process as disclosed, the cyclodextrin, derivative thereof, salt thereof, or combination thereof is an azidocyclodextrin or diazidocyclodextrin. In some embodiments, the diazidocyclodextrin is a diazido-α-cyclodextrin, diazido-β-cyclodextrin, or diazido-γ-cyclodextrin. In another embodiment of the process as disclosed, the azidocyclodextrin derivative is diazido-hydroxyalkyl-α-cyclodextrin, diazido-hydroxyalkyl-β-cyclodextrin, diazido-hydroxyalkyl-γ-cyclodextrin, or diazido-(2-hydroxypropy)-β-cyclodextrin. In still other embodiments, the diazidocyclodextrin derivative is diazido-hydroxyalkyl-α-cyclodextrin, diazido-hydroxyalkyl-β-cyclodextrin, diazido-hydroxyalkyl-γ-cyclodextrin, or diazido-(2-hydroxypropy)-β-cyclodextrin.

In a non-limiting embodiment, the cyclodextrin moiety in the process as disclosed includes, but is not limited to, β-cyclodextrin (β-CD), or its derivatives, wherein the derivatives are selected from the group consisting of α-cyclodextrin, hydroxypropyl β-cyclodextrin (HP-β-CD), sulfobutyl ether β-cyclodextrin (SBE-β-CD), methyl βcyclodextrin (Me-β-CD), γ-cyclodextrin, and other charged or uncharged derivatives of β-CD.

In other embodiments, the cyclodextrin moiety or a derivative thereof, is derived from β-cyclodextrin, (2-hydroxypropyl)-β-cyclodextrin, derivatives thereof, or combinations thereof. In one embodiment, the cyclodextrin is β-cyclodextrin or (2-hydroxypropyl)-β-cyclodextrin.

The present disclosure particularly provides a process of preparing polymers of cyclodextrin conjugates comprising repeating units of cyclodextrin moiety attached through a triazole-ketal-triazole linker [pBCDK polymer viz. (cyclodextrin-triazole-ketal-triazole)$_n$, wherein 'n' ranges from about 4 to 1000]. In the said process, the cyclodextrin units are conjugated via a triazole-ketal-triazole to afford the pBCDK polymer.

In a more specific embodiment of the present disclosure, the process of preparing the pBCDK polymer comprises steps of:
1. reacting a β-CD with biphenyl-4,4-disulfonylchloride to obtain a biphenyl-4,4'-disulfonate capped β-CD;
2. reacting a biphenyl-4,4'-disulfonatecapped β-CD with sodium azide to obtain a diazide derivative of β-CD; and
3. carrying out a click reaction (1,3-dipolar cycloaddition reaction) between a diazide derivative of β-CD and

Figure 3:
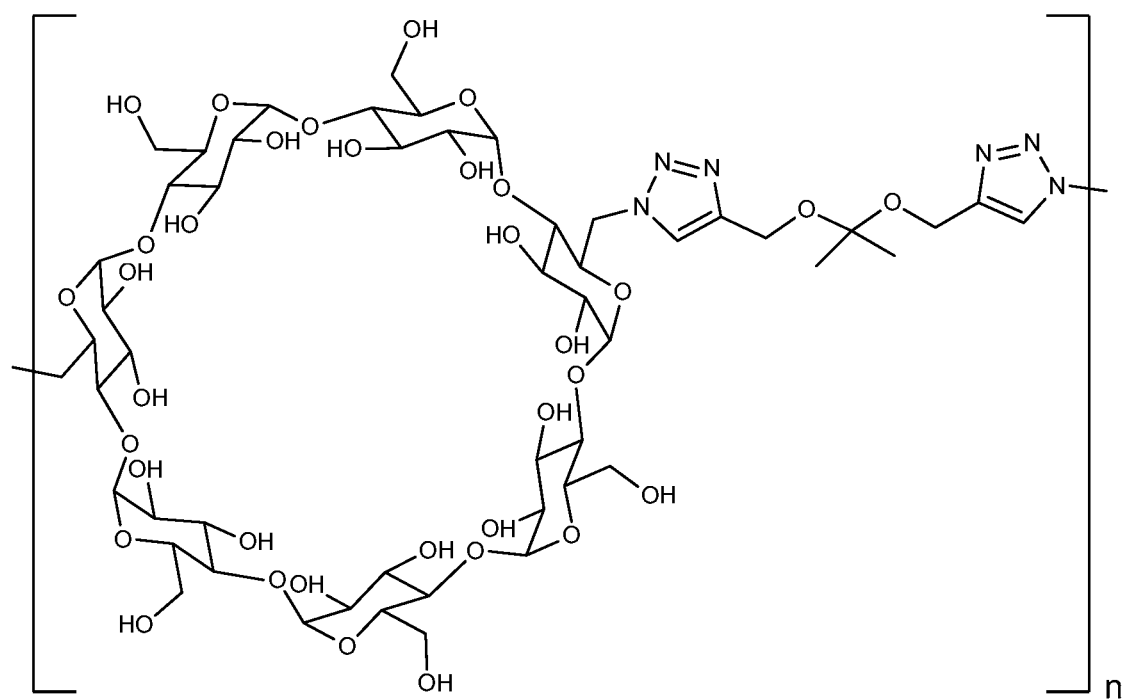
FIG. 3 depicts an exemplary pBCDK polymer structure (e.g., with repeating units of cyclodextrin-triazolyl-ketal-triazolyl) of present disclosure.

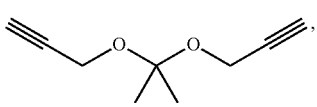

to obtain a pBCDK polymer such as that exemplified in FIG. 3.

In an embodiment of the above process, the diazide derivative of β-CD is a diazido-β-CD of the following structure:

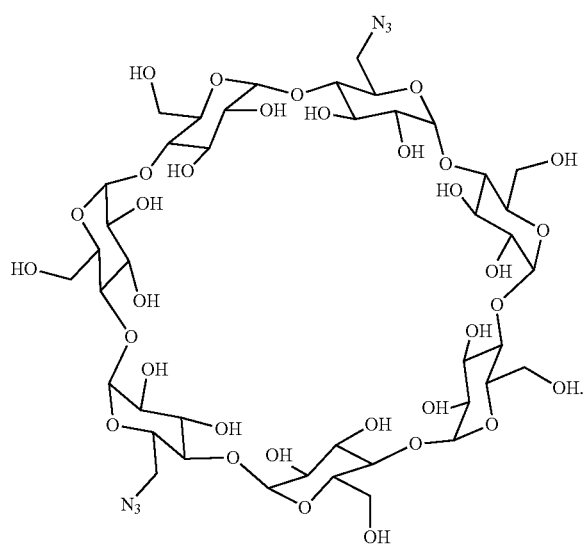 [SMILES: [N-]=[N+]=NCC1OC2OC3C(CO)OC(OC4C(CO)OC(OC5C(CN=[N+]=[N-])OC(OC6C(CO)OC(OC7C(CO)OC(OC8C(CO)OC(OC1C(O)C2O)C(O)C8O)C(O)C7O)C(O)C6O)C(O)C5O)C(O)C4O)C(O)C3O]

In an embodiment of the above processes of preparing polymers of cyclodextrin conjugates, the step-1 is optionally carried out in presence of solvent. In another embodiment, the solvent in step-1 is selected from the group consisting of pyridine, N,N-dimethylformamide, dimethyl sulfoxide and a combination thereof In an embodiment of the above processes of preparing polymers of cyclodextrin conjugates, the step-2 is optionally carried out in presence of metal halide. In another embodiment, the metal halide in step-2 is selected from the group consisting of potassium iodide, sodium iodide, and a combination thereof In an embodiment of the above processes of preparing polymers of cyclodextrin conjugates, the step-3 is optionally carried out in presence of solvent. In another embodiment, the solvent in step-3 is selected from the group consisting of N,N-dimethylformamide, dimethyl sulfoxide, tetrahydrofuran, toluene, water, and combinations thereof.

In an embodiment of the above processes, the linker (triazole-ketal-triazole) is formed in the final product (pBCDK polymer) via 1,3-dipolar cycloaddition reaction between alkyne moiety and azide of cyclodextrin.

In an embodiment of the above processes of preparing polymers of cyclodextrin conjugates, 1,3-dipolar cycloaddition reaction between alkyne moiety and azide of cyclodextrin is carried out in presence of a copper salt. In one embodiment, the copper salt is copper tris(triphenylphosphine) bromide, copper iodide, copper bromide, and combinations thereof.

In one embodiment, the copper salt is copper tris(triphenylphosphine) bromide.

In still another embodiment of the present disclosure, the above process of synthesizing polymers of cyclodextrin conjugates is carried out at a temperature ranging from about −78° C. to about 100 ° C., and for a time period ranging from about 1 hour to about 48 hours.

Having now generally described the invention, the same will be more readily understood through reference to the following examples, which are provided by way of illustration and are not intended to be limiting of the present invention.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

In addition, those of ordinary skill in the art recognize that some functional groups can be protected/deprotected using various protecting groups before a certain reaction takes place. Suitable conditions for protecting and/or deprotecting specific functional group, and the use of protecting groups are well-known in the art. For example, various kinds of protecting groups are described in T. W. Greene and G. M. Wuts, Protecting Groups in Organic Synthesis, Second edition, Wiley, New York, 1991, and other references cited above.

EXAMPLES
Example 1
Procedure for Synthesis of pBCDK Polymer
Step 1: Synthesis of biphenyl-4,4'-disulfonate-capped β-CD (2)
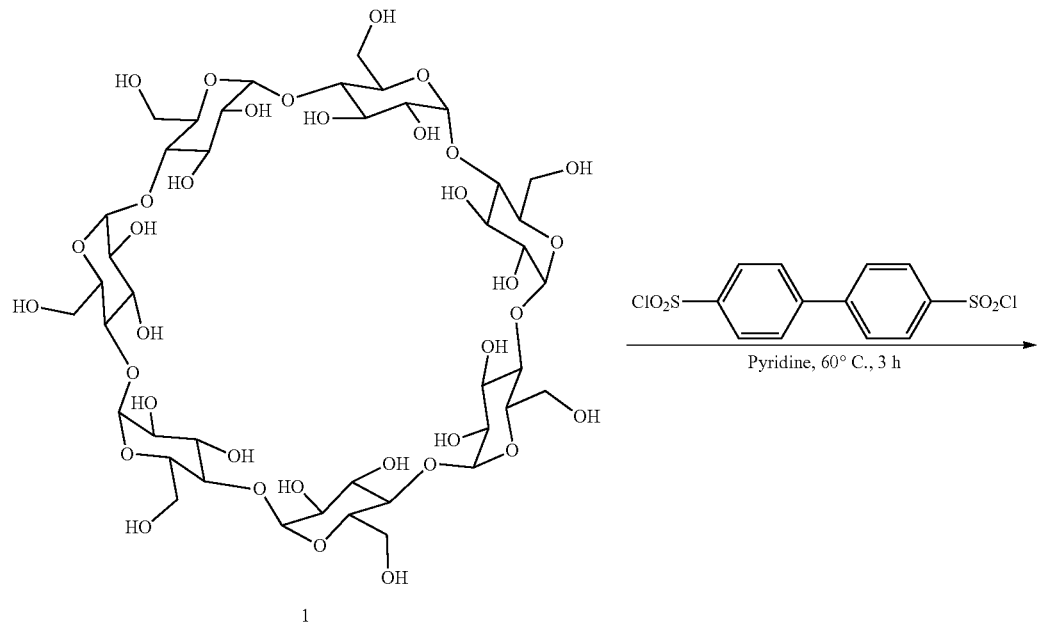
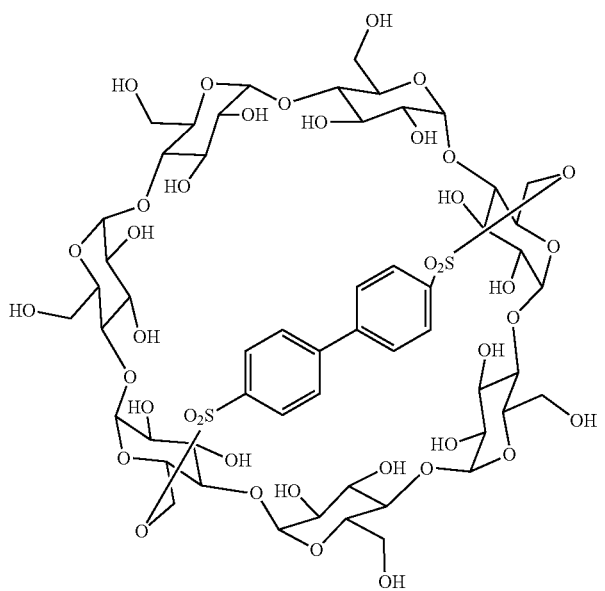

-continued
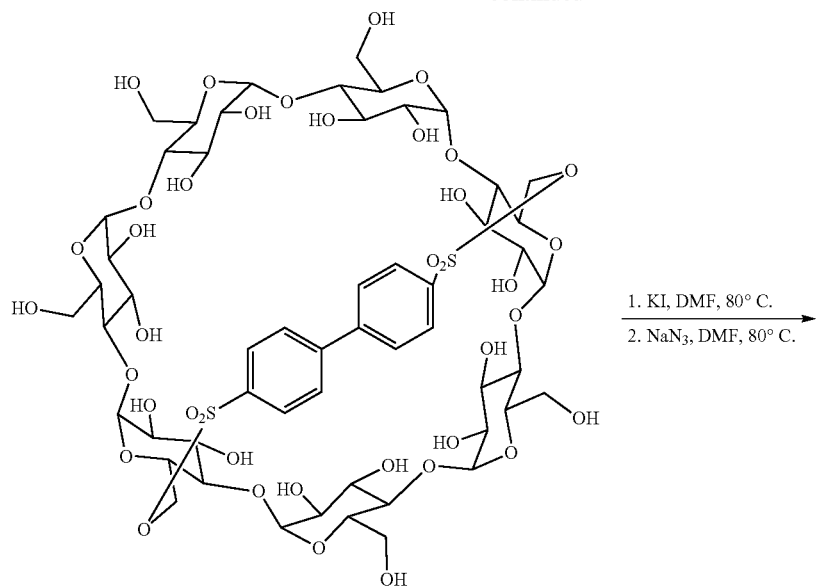
2
1. KI, DMF, 80° C.
2. NaN₃, DMF, 80° C.
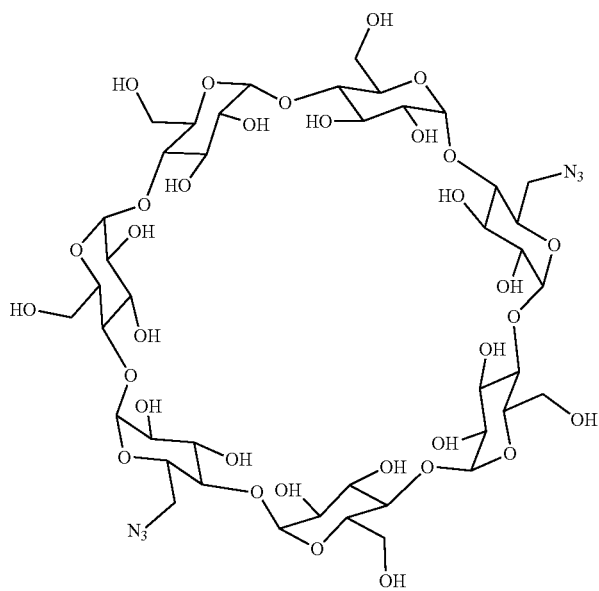
3

To a solution of dried β-cyclodextrin (10 g, 8.8 mmol, 1.0 equiv.) in 250 mL of freshly distilled pyridine, was added biphenyl-4,4'-disulfonyl chloride (2.78 g, 8.0 mmol, 0.9 equiv.) in four equal portions at 15 min intervals. The resulting solution was stirred at 60 °C. under nitrogen for an additional 3 h and subsequently the solvent was removed to dryness under vacuum to get sticky solid. The crude residue was dissolved in minimum quantity of water and the resulting solution was added drop wise to a 15% $H_2O$:ACN mixture (1 L) with vigorous stirring. The precipitate formed was filtered through Buchner funnel and subjected to column chromatography using a gradient elution of 10-20% water in acetonitrile. This procedure gave 5.8 g (46.7% yield) of β-CD(OTs)$_2$ (Compound 2). IR (KBr, cm$^{-1}$): 3407, 2910, 1658; $^1$HNMR (400 MHz, $D_2O$) δ 3.52-4.02 (m, 54H), 5.10 (s, 7H), 7.61-8.85 (8H).

Step 2: Synthesis of 6$^A$, 6$^D$-diiodo 6$^A$, 6$^D$-dideoxy β-cyclodextrin

To a solution of biphenyl-4,4'-disulfonate capped β-CD (5.8 g, 4.1 mmol, 1.0 equiv.) in 50 mL of anhydrous DMF was added dry potassium iodide (20.4 g, 123.1 mmol, 30.0 equiv.). The resulting solution was stirred at 80 °C. for additional 2 h. The mixture was allowed to cool to room temperature, and insoluble materials were removed by filtration. The solvent was evaporated to dryness under vacuum. The residue was then dissolved in 25 mL of water and 8 mL of tetrachloroethylene was added at 0° C. with vigorous stirring. The precipitate formed was filtered through Buchner funnel and washed with excess acetone. The precipitate was lyophilized to dryness afforded desired product which was used for the next step without further purification.

Step 3: Synthesis of 6$^A$, 6$^D$-diazido 6$^A$, 6$^D$-dideoxy β-cyclodextrin (3)

To a solution of 6$^A$, 6$^D$-diiodo 6$^A$, 6$^D$-dideoxy β-CD (8 g 5.8 mmol, 1 equiv.) in 50 mL of anhydrous DMF was added sodium azide (2.26 g, 34.8 mmol, 6 equiv.). The resulting suspension was stirred at 80° C. under nitrogen for additional 12 h. After completion of the reaction the solution was evaporated to dryness and the crude residue was subjected to column chromatography using water in acetonitrile. This procedure gave 1.8 g (25%) of β-CD(N$_3$)$_2$ (Compound 3). IR (KBr, cm$^{-1}$): 3366, 2037; $^1$HNMR (400 MHz, $D_2O$) δ 2.93 (s, 2H), 3.09 (s, 2H), 3.66-4.07 (m, 50H), 5.14 (s, 7H).

Step 4: Synthesis of 2,2-dipropergyloxy-propane (4)

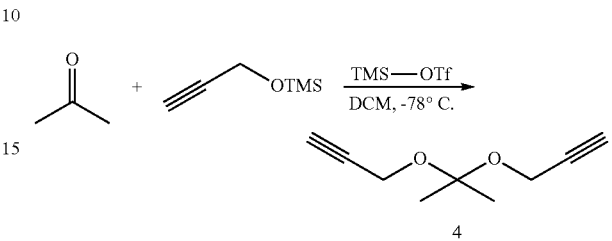

To a solution of acetone (1.43 mL, 19.5 mmol, 1 equiv.) and (propargyloxy)trimethylsilane (5 gm, 38.9 mmol, 2.0 equiv.) in dry dichloromethane under inert atmosphere at −78° C., trimethylsilyl trifluoromethanesulfonate (0.86 gm, 20 mol %) was added slowly. The reaction mixture was allowed to stir at same temperature for an additional 2.5 h. Pyridine (0.6 mL) was added to the reaction mixture and allowed to stir for further 15 min. Progress of the reaction was monitored by TLC. After completion of the reaction, the reaction mixture was poured in to the solution of saturated sodium bicarbonate and was extracted with diethyl ether. The collective organic layer was washed with brine and evaporated to dryness under reduced pressure. The crude residue was purified through column chromatography using hexane/EtOAc (95:05) as the eluent system to afford Compound 4 (2.2 g, 76%) as a colorless oil. $^1$HNMR (400 MHz, CDCl$_3$) δ 1.43 (s, 6H), 2.41 (t, J=2.4 Hz, 2H), 4.16 (d, J=2.7 Hz, 4H); $^{13}$C NMR (100 MHz, CDCl$_3$):δ 24.62, 49.36, 73.46, 80.46, 101.51.

Step 5: Click reaction to synthesize pBCDK polymer

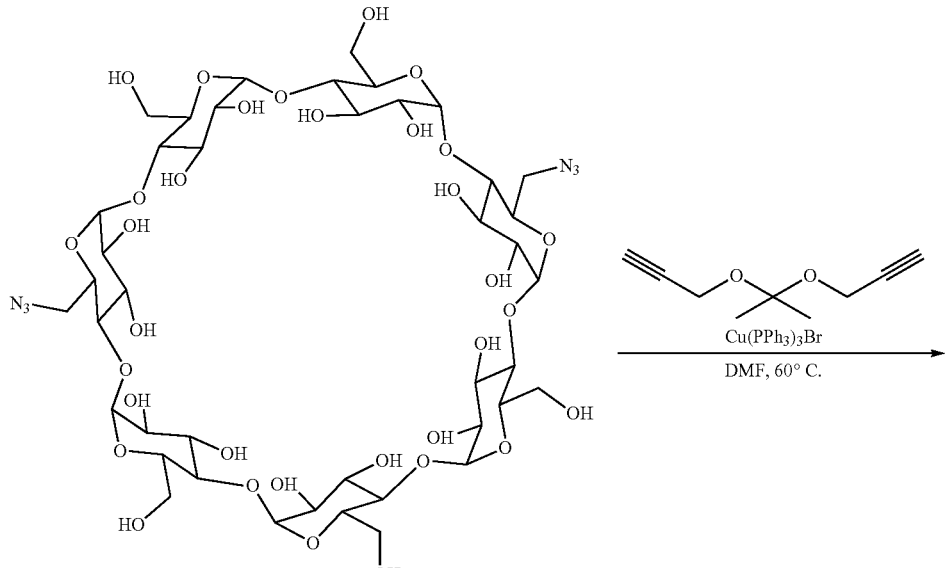

-continued

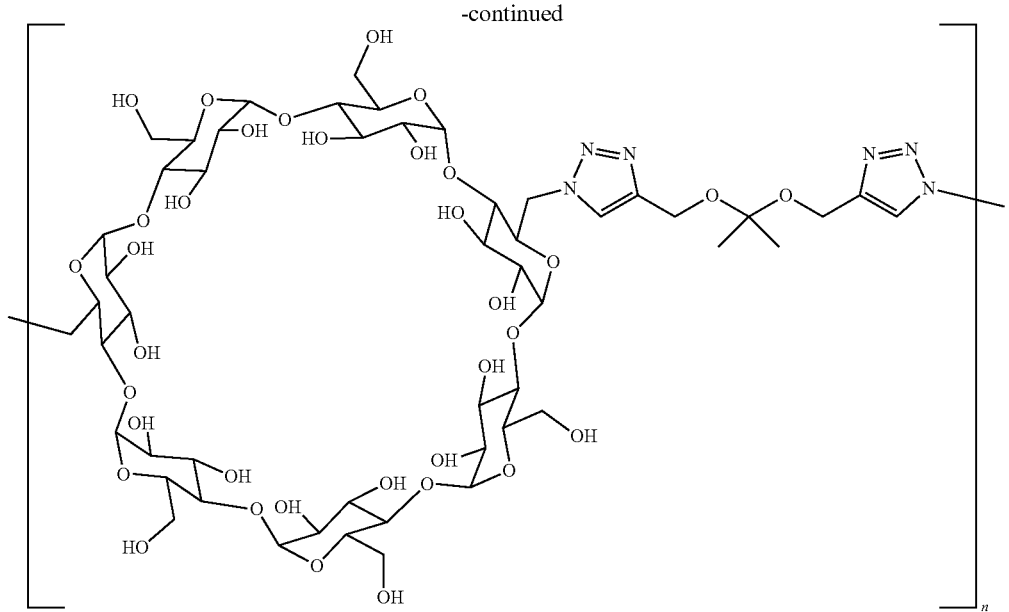

wherein n ranges from 4 to 1000.

General Procedure: To a degassed solution of 3 in solvent (DMF or DMF:H$_2$O 1:1 or THF:H$_2$O 1:1), 4 and Cu (PPh$_3$)$_3$Br (5 mol %) is added. The solution is stirred with heating at 60° C. for about 24 hours. The viscous solution is poured into a large excess of ethyl acetate (hexane or acetone or diethyl ether) (10× of reaction volume). The resulting precipitate is removed by centrifugation. The solid product is re-dissolved and re-precipitated in (acetone, hexane, or ethyl acetate) respectively. The same process is continued for about 3 times to achieve an off white powder i.e., pBCDK polymer. The molecular weight of the pBCDK polymer is determined by gel permeation chromatography (GPC) in DMF.

Polymer A—X is Approximately 17

Figure 4:
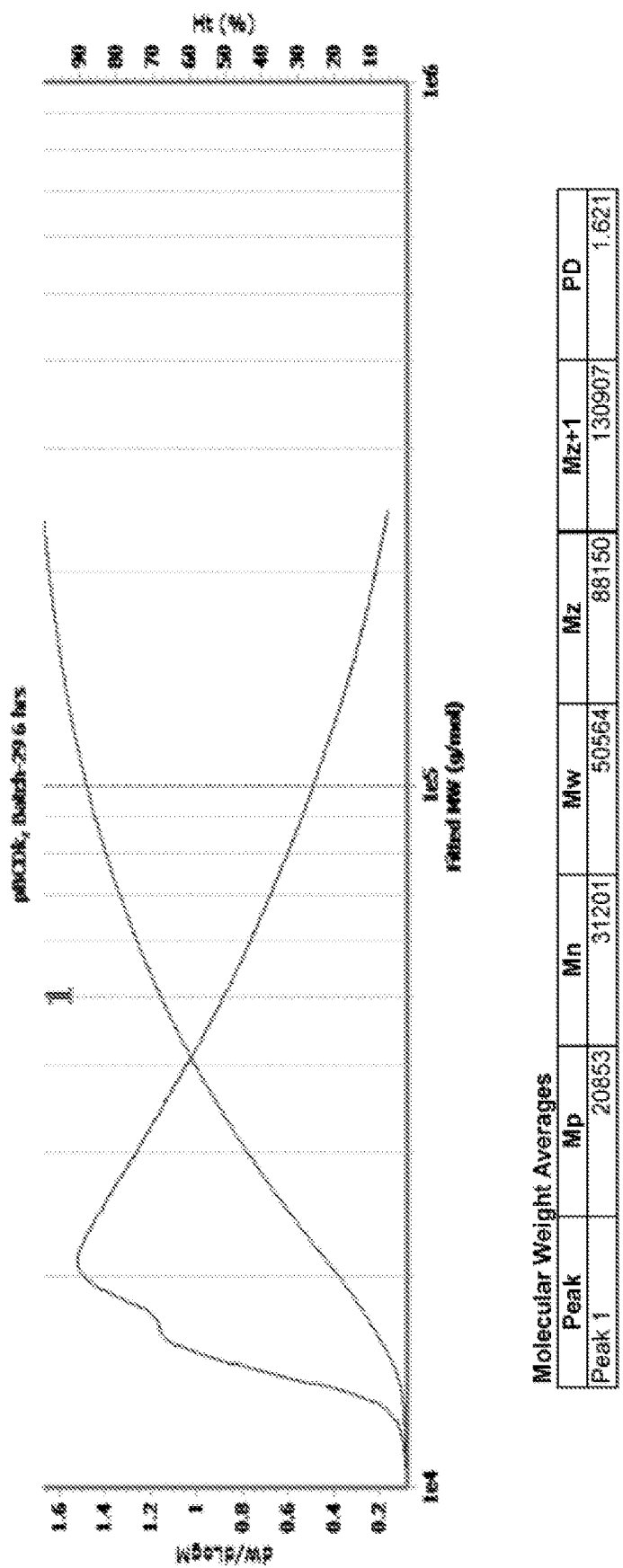
FIG. 4 shows a gel permeation chromatograph of Polymer A.
Figure 5:
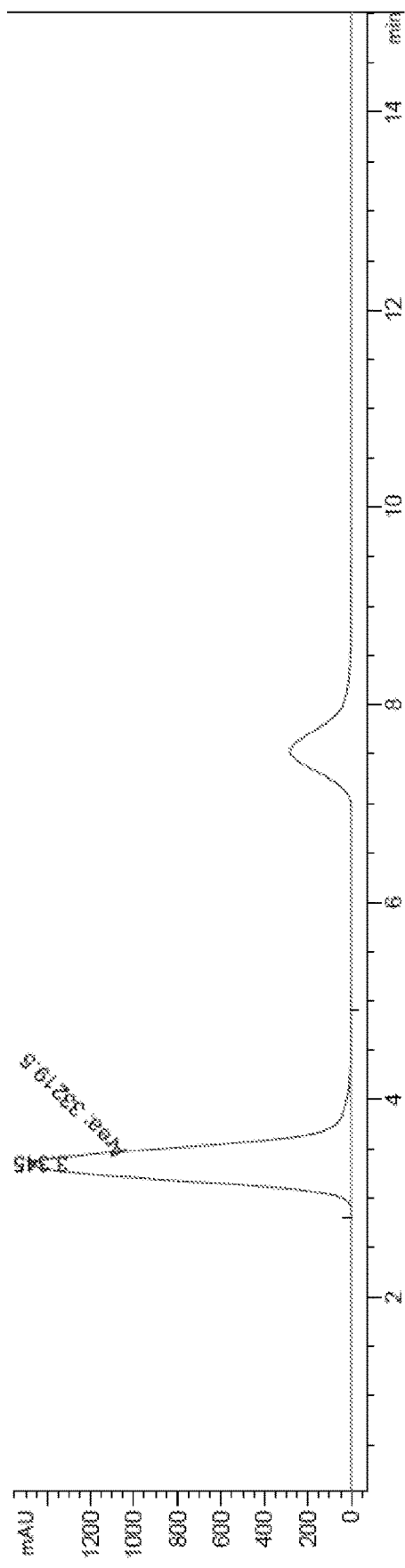
FIG. 5 shows an HPLC analysis of Polymer A.

Polymer A was synthesized according to the general procedure discussed above, employing 1 g of 3 and 128 mg of 4. The reaction was allowed to proceed for 6 h. Polymer A has a molecular weight peak (Mp) of 20,853 g/mol and a polydispersity index (PDI) of 1.621. Polymer A was characterized with GPC (FIG. 4) and HPLC (FIG. 5).

Polymer B—X is Approximately 25

Figure 6:
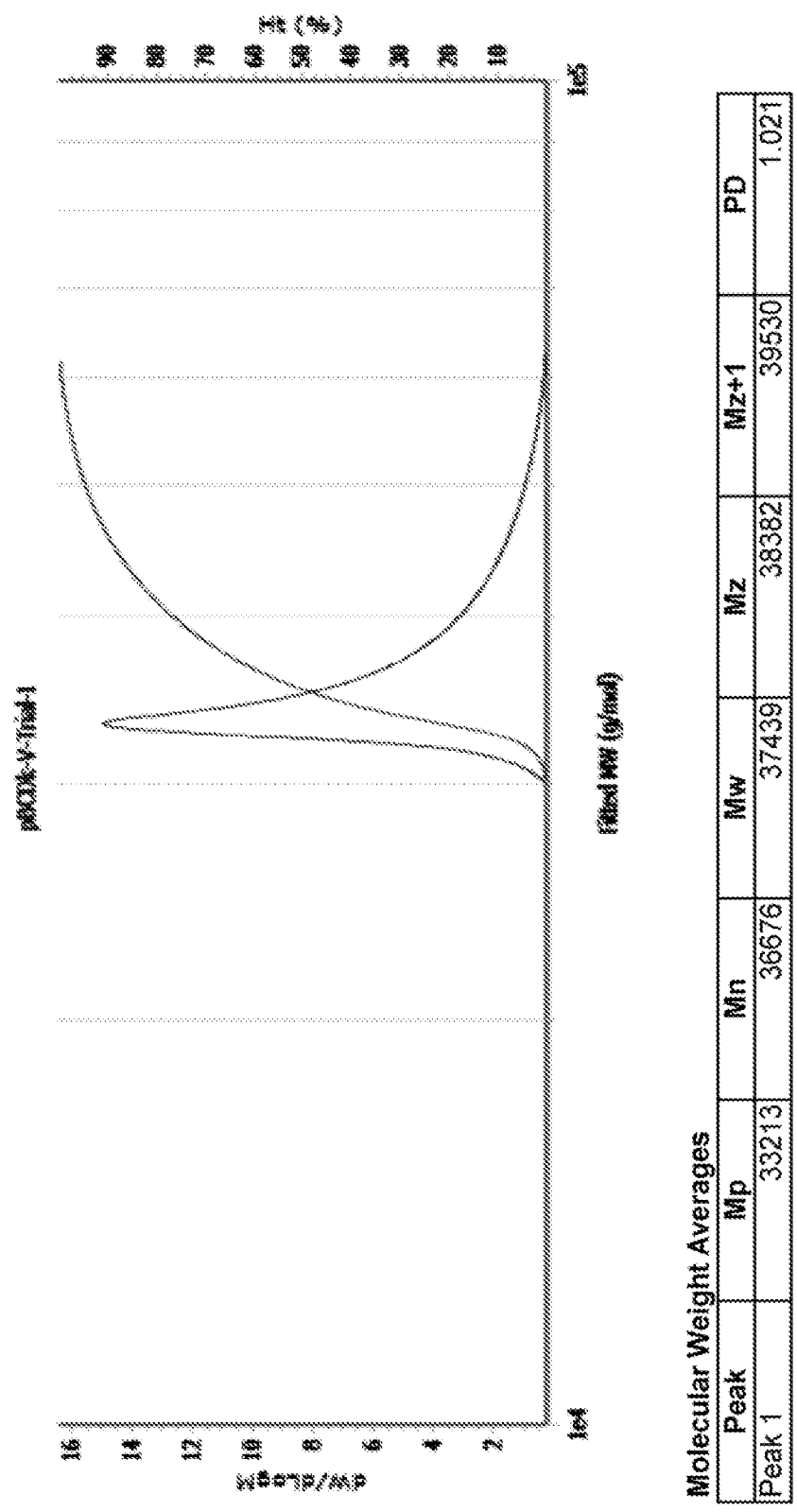
FIG. 6 shows a gel permeation chromatograph of Polymer B.
Figure 7:
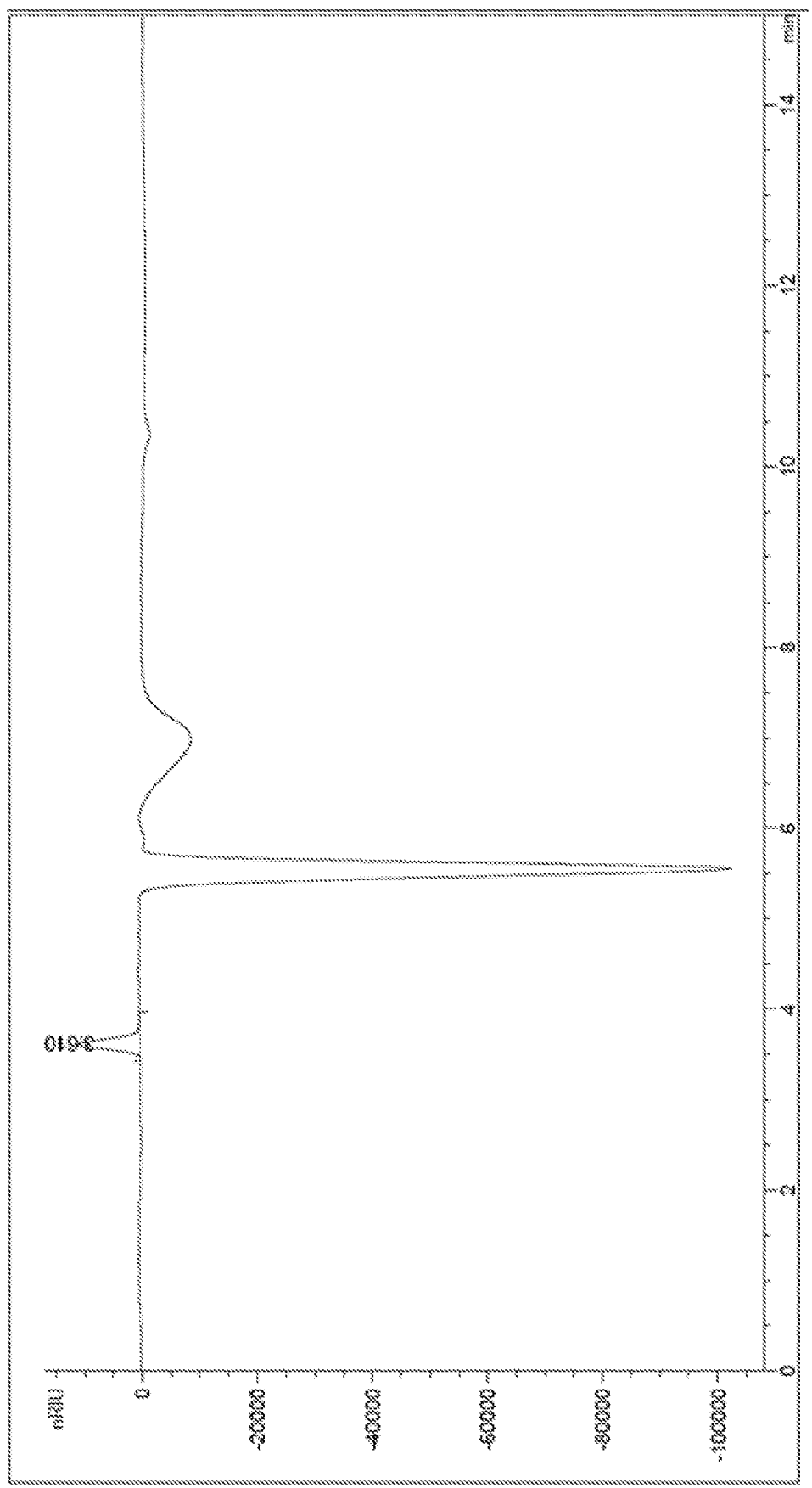
FIG. 7 shows an HPLC analysis of Polymer B.
Figure 8:
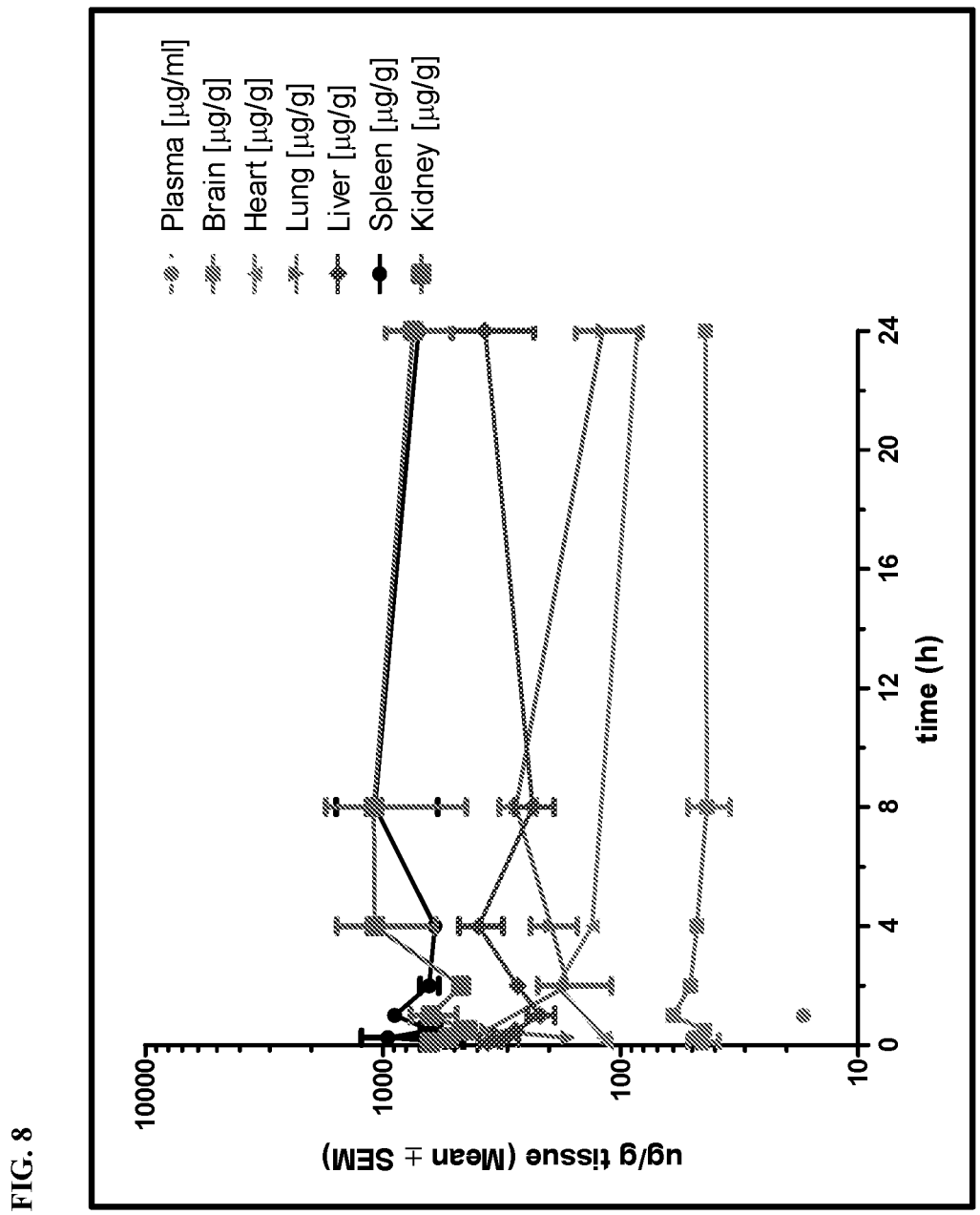
FIG. 8 shows biodistribution profile of Polymer B in mice after subcutaneous administration.

Polymer B was synthesized according to the General Procedure discussed above, employing 1 g of 3 and 128 mg of 4. The reaction was allowed to proceed for 24 h. Polymer B has a molecular weight peak (Mp) of 33,213 g/mol and a polydispersity index (PDI) of 1.021. Polymer B was characterized with GPC (FIG. 6) and HPLC (FIG. 7).

Example 2

Subcutaneous Administration of Polymer B in Mice

Figure 9:
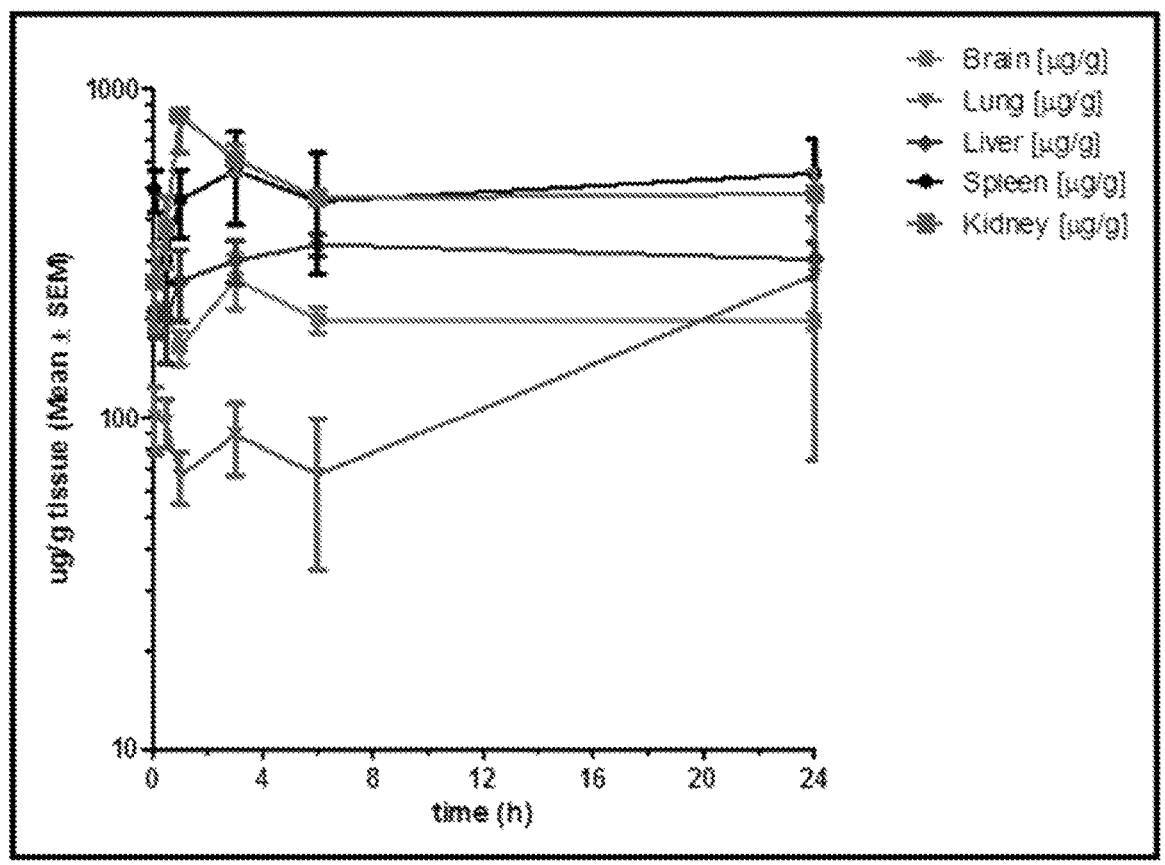
FIG. 9 shows biodistribution profile of Polymer B in mice via intranasal administration.

An HPLC-UV based bioanalytical method was developed in mouse plasma for Polymer B. The method was linear between 13.4 and 500 µg/ml plasma, with an LLOQ of 13.4 µg/ml, was precise and accurate. The recovery was >90% from plasma and tissues. The PK and tissue distribution of pBCDK was performed in mice following a single subcutaneous dose of 100 mg/kg. The concentration of Polymer B in various cells were monitored over 24 h. Uptake and retention of Polymer B A in organs including brain, lungs, liver, spleen, and kidney were observed (FIG. 9). Error bars in FIG. 9 are SEM.

Example 3

Dose Response/Frequency Studies in Focal Segmental Glomerulosclerosis

Figure 10:
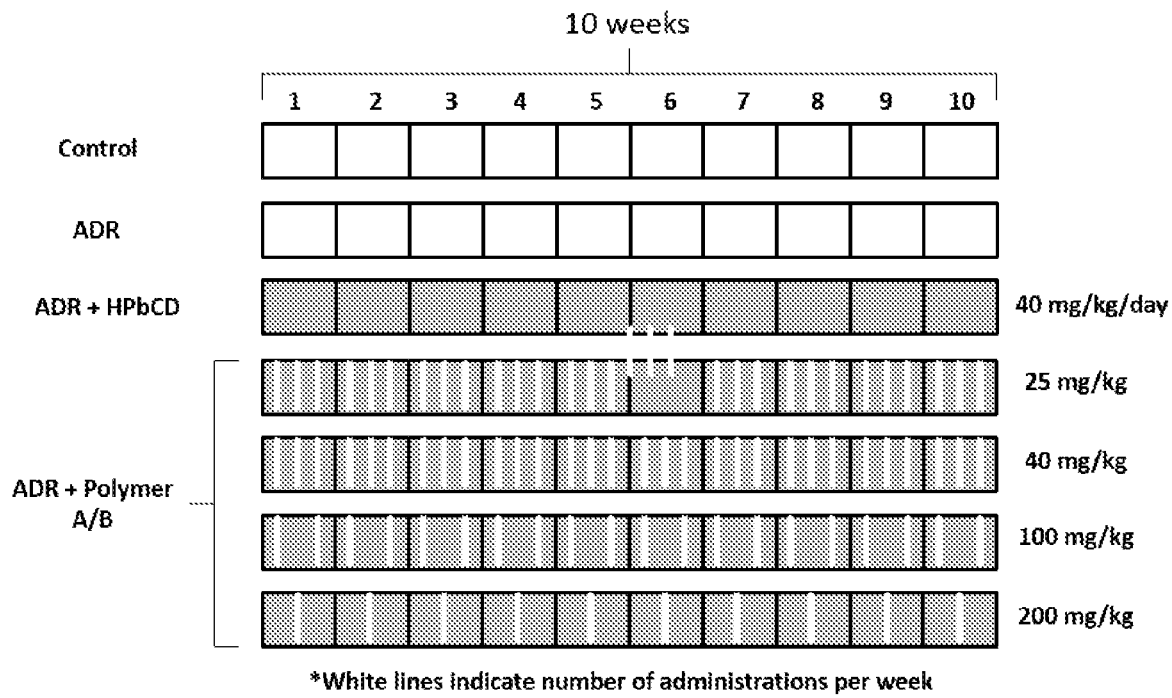
FIG. 10 summarizes the dose response/frequency studies used in the Focal Segmental Glomerulosclerosis (FSGS) animal model study comparing controls, reference, and test compounds.

Experimental Protocol: 6 animals (BALB/c mice) per group of 6-7 weeks of age were used. Nephropathy was induced in all animals, except group 1 (normal control), with Adriamycin (ADR, 11 mg/kg, i.v., single dose) at dose volume of 6 ml/kg. Normal saline (0.9%) was used as vehicle for the reference and test compounds. Treatment was started 24 hours after Adriamycin injection. Groups of animals (n=6) were treated subcutaneously with vehicle, HBCD, Polymer A and Polymer B at the doses and regimens shown in FIG. 10, for 10 weeks. At the end of the study, animals were sacrificed by CO$_2$ exposure, blood samples and kidneys were collected for the estimation of various biomarkers in serum.

Figure 11:
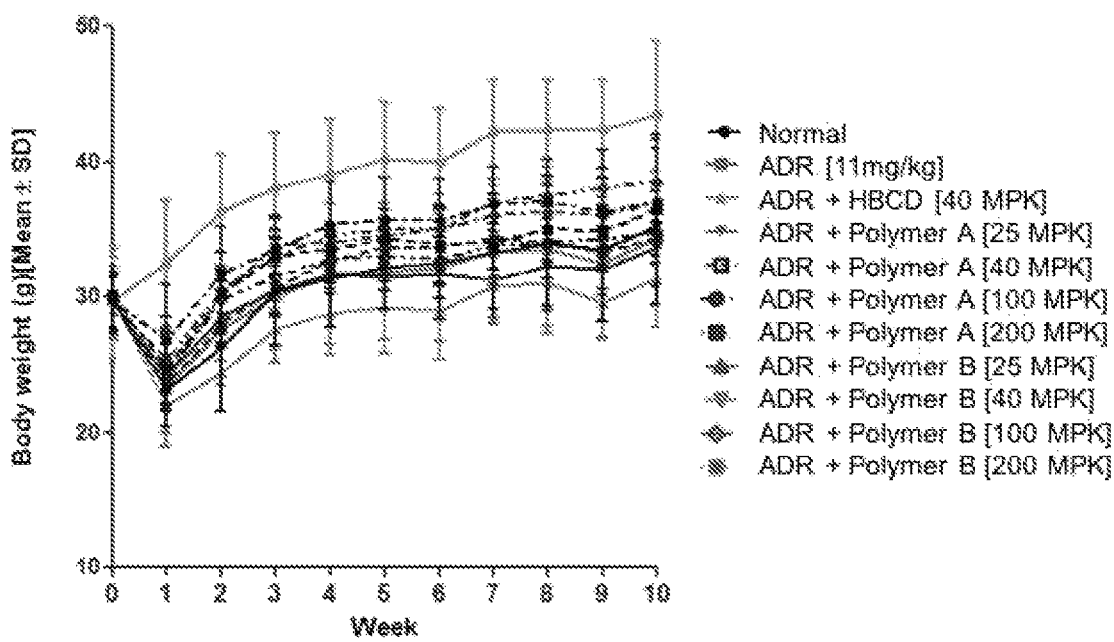
FIG. 11 is a graph of the mean weekly body weight of mice during and at the end of treatment with reference and test compounds over several doses. Error bars indicate the mean±SD.

Body weights: Body weights were measured at the beginning of study and weekly throughout for ten weeks (FIG. 11) to provide a general assessment of rodent health after therapy. Mice treated with ADR/HBCD (hydroxypropyl β-cyclodextrin, 40 mg/kg/day) fared the worst out of all the test groups when compared to normal mice (vehicle only), displaying the largest drop in mean body weight without any substantial rebound. In contrast, mice treated with a single dose of 200 MPK of Polymer A (highest dose delivered) demonstrated the most substantial weight-gain of the treatment groups, indicative of animals in better overall health. This result was closely followed by the mice dosed with either 100 MPK of Polymer A or 100 MPK of Polymer B, each group of animals possessing about the same mean body weight at the completion of the study. However all the test groups with Polymer A and Polymer B responded with better weight-gain than with the HBCD positive control, highlighting the improved tolerability and/or efficacy of these novel agents in comparison to the HBCD treatment option. The overall results suggest that polymers of the present disclosure are tolerated at higher doses, providing a range of potential options for treating kidney diseases such as Focal Segmental Glomerulosclerosis (FSGS).

Figure 12:
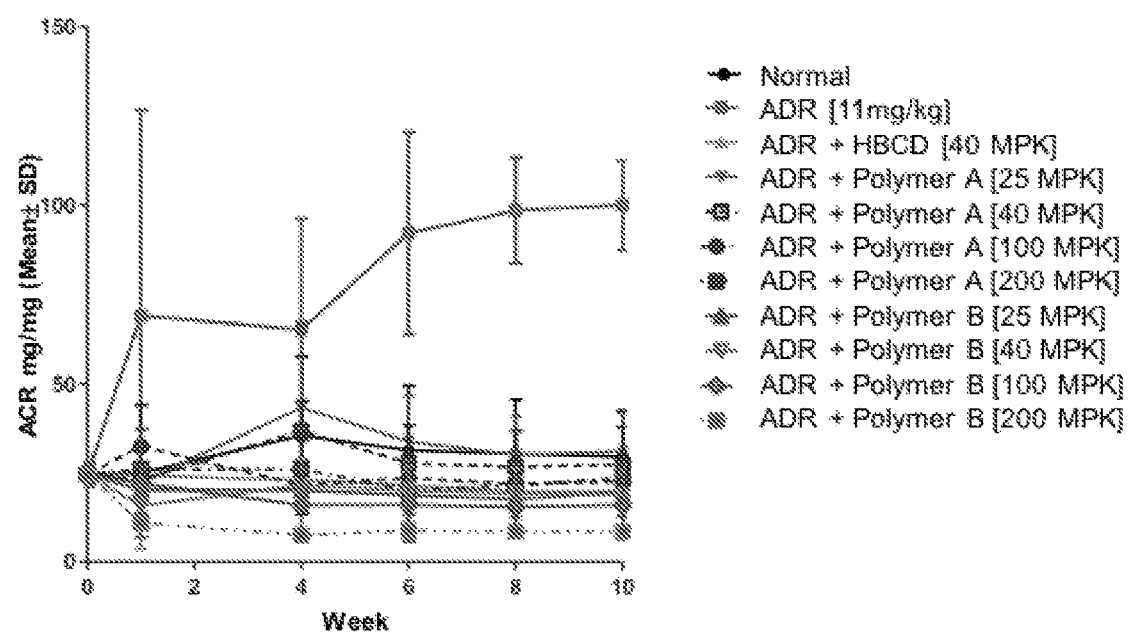
FIG. 12 is a graph of the mean albumin to creatinine ratio (ACR) in mice during and at the end of treatment with reference and test compounds at several doses. Error bars indicate the mean±SD.

ACR Ratios from Analysis of Urine: On day 0 six animals were fasted and urine samples were taken collected to determine the baseline Albumin/Creatinine ratio (ACR) prior to Adriamycin injection. At end of week 1, 4, 6, 8 and 10 urine samples were taken from all the animals to determine Albumin/Creatinine ratio (FIG. 12). Urine samples were analysed for Albumin and Creatinine in an Automated Clinical Chemistry Analyzer EM360, Transasia Bio-medicals Ltd. Albumin was analysed by using the BCG Dye method with an Erba standard albumin kit. Creatinine was analysed by Jaffe's method with Erba standard Creatinine kit. Kidney function impaired by injection with ADR as a surrogate for early-stage kidney disease showed a gradual increase in the albumin/creatinine ratio as expected. However, treatment with Polymer A and Polymer B at all dosing levels and schedules restored the ACR ratio to at or below normal levels, an indication that mice kidneys were functioning properly. The results suggest that the polymers of the present disclosure are particularly useful at lower concentrations and lower frequency of administrations than hydroxypropyl β-cyclodextrin, thereby providing viable alternatives for treatment of kidney diseases with potentially diminished side-effects.

Serum Analysis: Serum samples were analysed in an Automated Clinical Chemistry Analyzer EM360, Transasia Bio-medicals Ltd, for albumin and creatinine.

Figure 13:
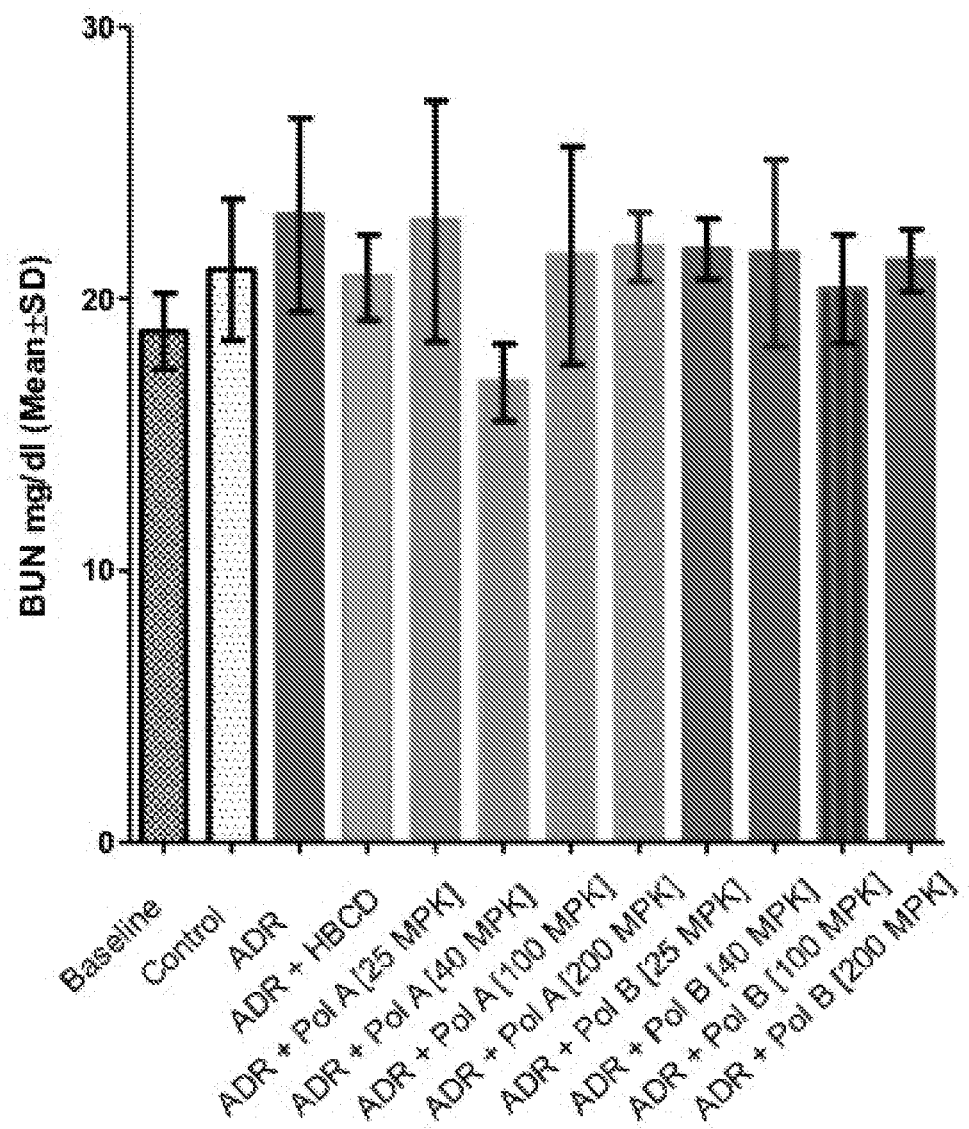
FIG. 13 is a graph of the mean serum blood urea nitrogen level (BUN) in mice following treatment with reference and test compounds at several doses. Error bars are mean±SD.

(a) Blood Urea Nitrogen (BUN) assay to assess the level of kidney function was analysed by the GLDH Urease method using an Erba standard BUN kit. (FIG. 13). Administration of ADR to induce nephropathy increased blood urea nitrogen levels as one would expect from an impaired kidney. Subsequent treatment with hydroxypropyl β-cyclodextrin (positive control, 40 mg/kg/day) appears to modestly restore function at the end of the study such that BUN levels return to that found for the control group. While various dosing regimens with Polymer A and Polymer B were marginally effective in this assay, dosing mice with 40 mg/kg three times per week of Polymer A led to a substantial reduction in BUN levels to below baseline, indicating a significant enhancement of waste product removal by the kidneys. Lower dosing compared to positive control (120 mg/kg/wk overall vs. 280 mg/kg/wk overall) indicates better maintenance of adequate drug concentrations, possible due a decrease in hydrophilicity that reduces clearance from the body.

Figure 14:
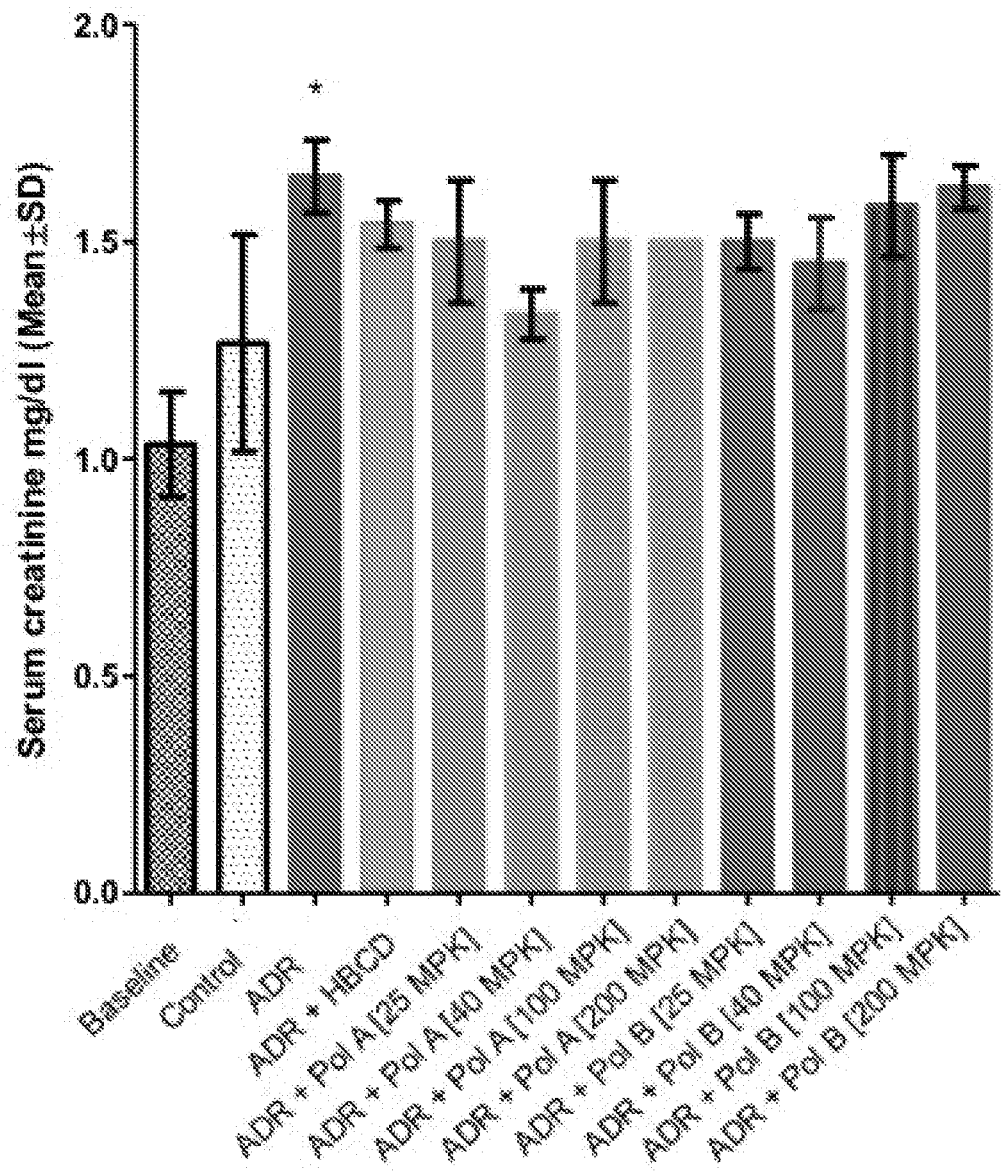
FIG. 14 is a graph of the mean serum creatinine level in mice following treatment with reference and test compounds at several doses. Error bars are mean±SD.

(b) Creatinine was analysed by using Jaffe's method with an Erba standard Creatinine kit (FIG. 14) to assess the level of kidney impairment after treatment with Polymer A and Polymer B. A similar trend was observed for serum creatinine as was observed for BUN levels described above. While creatinine was elevated in all treatment groups compared to baseline and control, Polymer A mice dosed at 40 mg/kg three times per week saw a significant decrease in serum creatinine, well below the amount found for HBCD treated mice, despite the lower dosing amount. The combination of data from these studies serves to illustrate the potential of the polymers of the present disclosure as treatment options for kidney disease compared to known cholesterol clearance compounds.

Example 4

Histopathology Images for Normal Mice, Control Groups, Mice Injected with Polymer A, and Mice Injected with Polymer B Histopathology: At the end of the study, kidney samples were collected from each animal, fixed in 10% NBF (Neutral Buffered Saline) and subjected to histopathology. Periodic acid-Schiff (PAS) or Hematoxylin and Eosin (H/E) staining of 4 micron-thick tissue sections was performed according to the standard protocols. Mesangial expansion area was determined based on the area of PAS staining.

Figure 15:
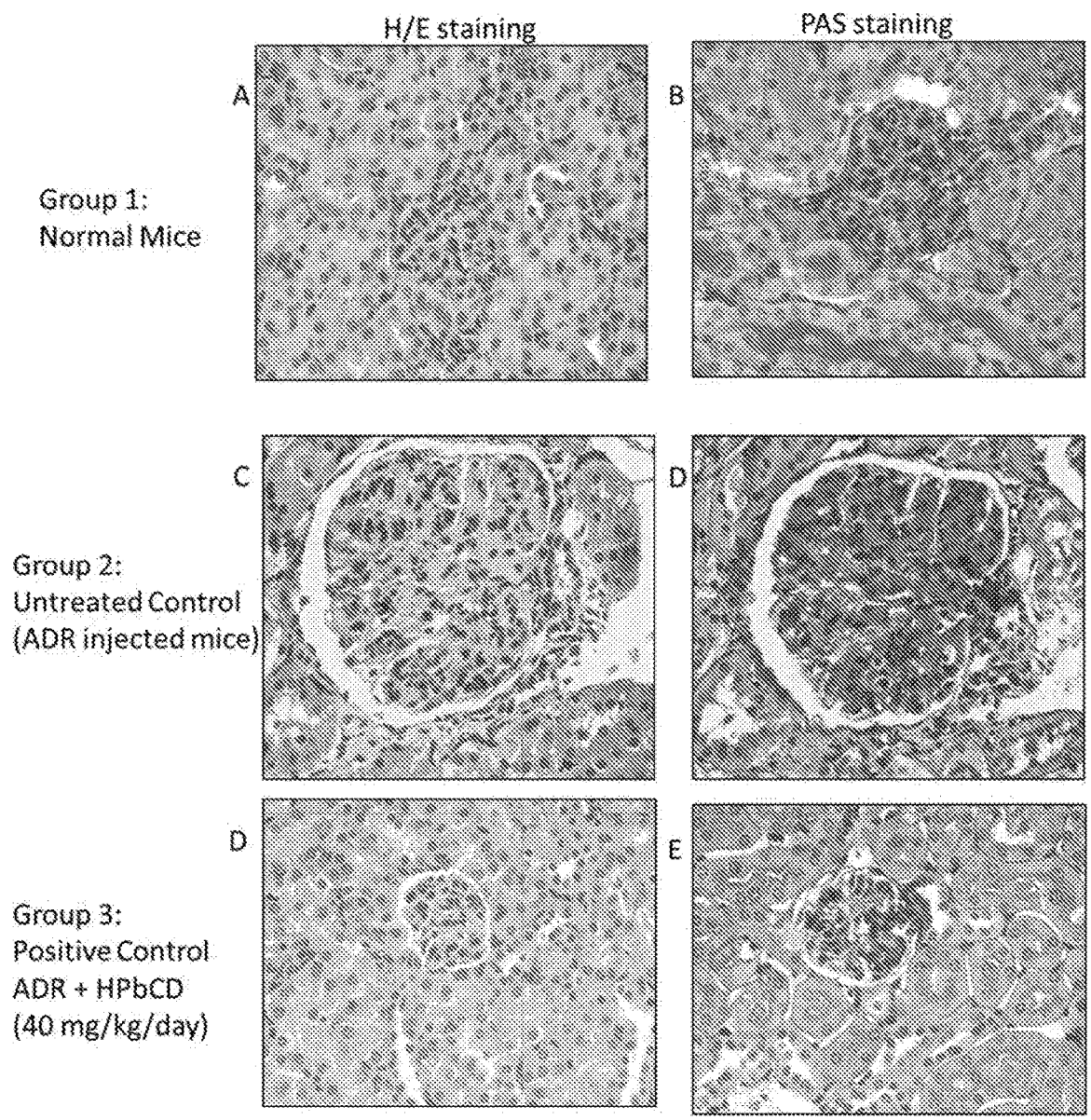
FIG. 15 shows kidney tissue samples subjected to histopathology for normal mice (Group 1), untreated control (Group 2, Adriamycin injected mice), and positive control (Group 3, ADR+HPbCD @ 40 mg/kg/day).

FIG. 15, group 1 shows the histopathology of normal mice glomeruli under two types of staining, H/E and PAS. Induction of nephropathy (kidney disease) with ADR results in a significant expansion of the mesangial area as illustrated by group 2 mice. However, the positive control (group 3) consisting of treatment with cholesterol-clearance compound, HBCD at 40 mg/kg/day, is able to counter the deleterious effects of ADR, maintaining glomeruli that are normal in appearance.

Figure 16:
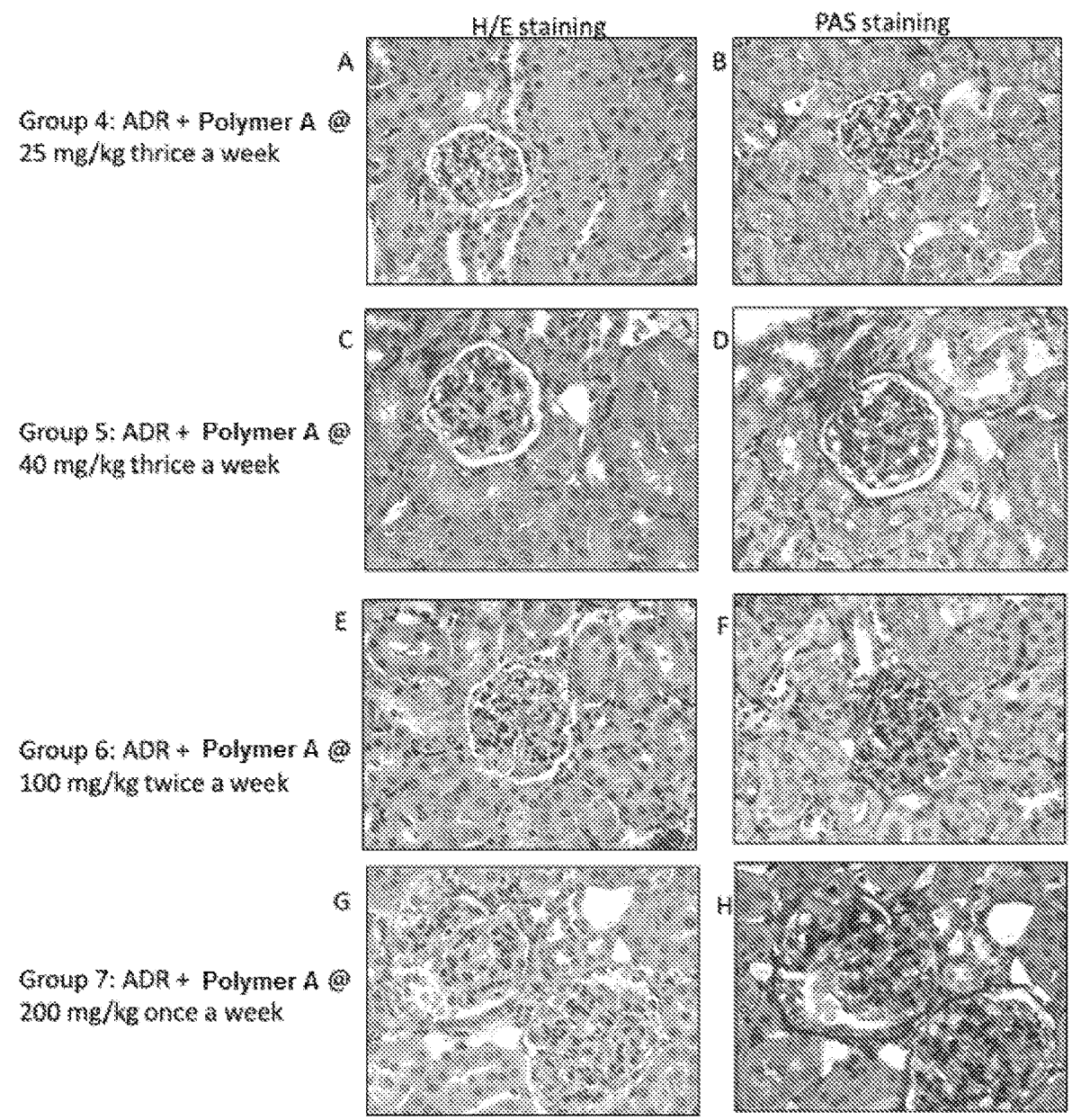
FIG. 16 shows kidney tissue samples subjected to histopathology for ADR+Polymer A @ 25 mg/kg thrice a week (Group 4, A and B), ADR+Polymer A @ 40 mg/kg thrice a week (Group 5, C and D), ADR+Polymer A @ 100 mg/kg twice a week (Group 6, E and F), and ADR+Polymer A @ 200 mg/kg once a week (Group 7, G and H).
Figure 17:
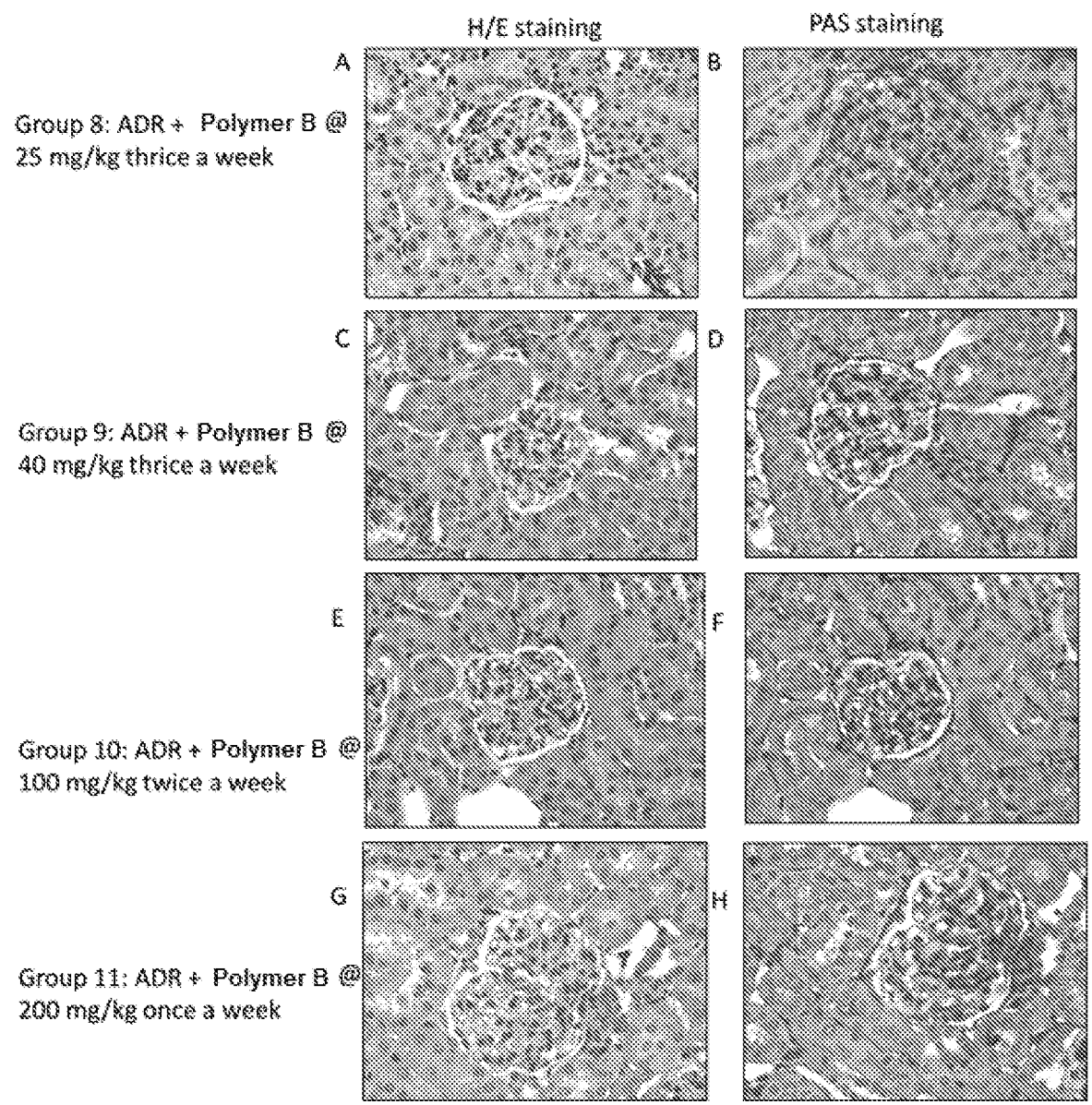
FIG. 17 shows kidney tissue samples subjected to histopathology for ADR+Polymer B @ 25 mg/kg thrice a week (Group 8, A and B), ADR+Polymer B @ 40 mg/kg thrice a week (Group 9, C and D), ADR+Polymer B @ 100 mg/kg twice a week (Group 10, E and F), and ADR+Polymer B @ 200 mg/kg once a week (Group 11, G and H).

The beneficial effects on glomeruli in mice treated with various doses of Polymer A is shown in FIG. 16. At the lowest dose of 25 mg/kg three times per week, the kidney microphotograph displayed glomeruli of normal appearance. No expansion of the mesangial area is observed, indicating the therapeutic benefits to nephropathic mice. Similar results were achieved at higher doses as the histopathology images were normal for group 5 (40 mg/kg three times per week) and group 6 (100 mg/kg twice per week) as well. A comparison of group 6 and group 7 mice shows the effects the dosing regimen has on treating nephropathy. Even though the total dose for both groups was the same, group 7 mice receiving a single injection of 200 mg/kg of Polymer A did not respond to treatment as well as group 6 mice receiving 100 mg/kg of Polymer A twice per week. Histopathology images from group 7 mice were much improved vs. the negative control, but still showed a minimal expansion of the mesangial area characteristic of mild nephropathy.

The histopathology studies described above were repeated for Polymer B, much to the same effect. Group 8 mice receiving the low dose of 25 mg/kg three times per week showed a dramatic improvement compared to the negative control as the kidney microphotograph showed glomeruli of normal appearance. For Polymer B, all the remaining treatment groups (9-11) completely countered the ADR-induced nephropathy, including the single dose of 200 mg/kg/wk given to group 11 mice.

Without being bound by any theory, the results suggest that Polymer A and Polymer B have improved physicochemical properties that function in reducing the rapid clearance that hinders the viability of more hydrophilic molecules like HBCD. While HDCD was dosed daily at 40 mg/kg, the pBCDK polymers proved to be efficacious at a range of less demanding dosing schedules. Polymer A and Polymer B proved quite capable of treating nephropathy at multiple low to moderate doses, as well as a weekly single injection, indicating that effective concentrations of Polymer A and Polymer B are likely maintained across the various dosing regimens. Alleviating the need for high concentrations/doses of these cholesterol-clearing drugs is a highly desirable attribute that should allow for optimization of the therapeutic benefits with minimization of any observed dose-dependent toxicity. Based on their improved properties, the polymers of the present disclosure afford significant benefits in treating kidney diseases such as Focal Segmental Glomerulosclerosis (FSGS), Diabetic Kidney Disease, Alport Syndrome, Minimal Change Kidney Disease, and Minimal Change Nephropathy over currently utilized cholesterol clearance compounds.

Additional embodiments and features of the present disclosure will be apparent to one of ordinary skill in art based upon description and examples provided herein. However, the examples above should not be construed to limit the scope of the present disclosure.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments in this disclosure have been described in terms of different embodiments, those skilled in the art will recognize that the embodiments herein can be practiced with modification within the spirit and scope of the embodiments as described herein.

Thus, the present disclosure introduces polymers of cyclodextrin conjugates, particularly pBCDK polymers, corresponding methods and applications wherein said polymers possess improved properties including but not limiting to longer circulation time, prolonged duration of action, improved biocompatibility, improved efficacy for removing cholesterol from the cells/treating lipid storage disorders, ease of administration/ effective route of administration leading to increased patient compliance, increased uptake in the brain leading to higher neuroprotection efficacy, lower doses, lower number of administrations of the polymer or composition thereof, and lower side effects.

The publications discussed herein are provided solely for their disclosure prior to the filing date of the present application. Nothing herein is to be construed as an admission that the present invention is not entitled to antedate such publication by virtue of prior invention.

While the invention has been described in connection with proposed specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for treating a kidney glomerular disease, the method comprising administering to a subject in need thereof, an effective amount of a cyclodextrin polymer having the following structure:

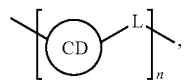

wherein

CD is a cyclodextrin moiety or a derivative thereof;

L is a linker moiety, wherein L comprises the following structure:

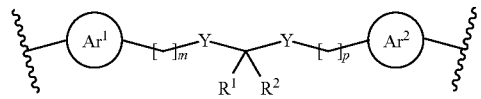

wherein $Ar^1$ and $Ar^2$ are each independently a 5- or 6-membered heteroaryl comprising 1, 2, 3 or 4 heteroatoms individually selected from N, O, and S, wherein $Ar^1$ and $Ar^2$ are optionally substituted with 1 to 3 $R^3$ groups;

Y is independently O, S, or $NR^4$;

m and p is each independently an integer from 1 to 10;

$R^1$ and $R^2$ are each independently $R^4$, $OR^4$, $SR^4$ or $R^1$ and $R^2$ taken together with the carbon atom to which they are attached form a double bonded O, S, or $NR^4$;

$R^3$ is selected from the group consisting of H, $C_1$-$C_3$ alkyl, $C_1$-$C_3$ alkyl sulfide, hydrazine, amine and halogen; and $R^4$ is H or a saturated or unsaturated $C_1$-$C_{10}$ linear alkyl, saturated or unsaturated $C_1$-$C_{10}$ branched alkyl, or saturated or unsaturated $C_1$-$C_{10}$ cycloalkyl, each of which is optionally substituted; and n is from 4 to 1000.

2. The method of claim 1, wherein the cyclodextrin moiety or a derivative thereof is selected from the group consisting of α-cyclodextrin, β-cyclodextrin, γ-cyclodextrin, hydroxyalkyl-α-cyclodextrin, hydroxyalkyl-β-cyclodextrin, hydroxyalkyl-γ-cyclodextrin, (2-hydroxypropyl)-β-cyclodextrin derivatives thereof, a salt thereof, a solvate thereof, and combinations thereof.

3. The method of claim 2, wherein the alkyl of the hydroxyalkyl cyclodextrin is selected from the group consisting of $C_1$-$C_{10}$ linear alkyl, $C_1$-$C_{10}$ branched alkyl, and $C_1$-$C_{10}$ cycloalkyl, each further comprising one or more optional substituents, wherein the one or more optional substituents are selected from methyl, ethyl and butyl.

4. The method of claim 1, wherein Y is O, m and p are both 1, $R^1$, $R^2$ and $R^3$ are each $C_1$-$C_3$ alkyl, and $Ar^1$ and $Ar^2$ are each triazole.

5. The method of claim 1, wherein L comprises the following structure:

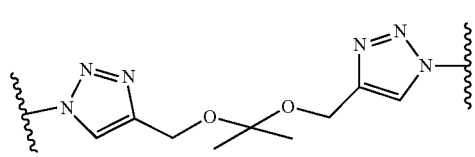

6. The method of claim 1, wherein the cyclodextrin polymer has the following structure

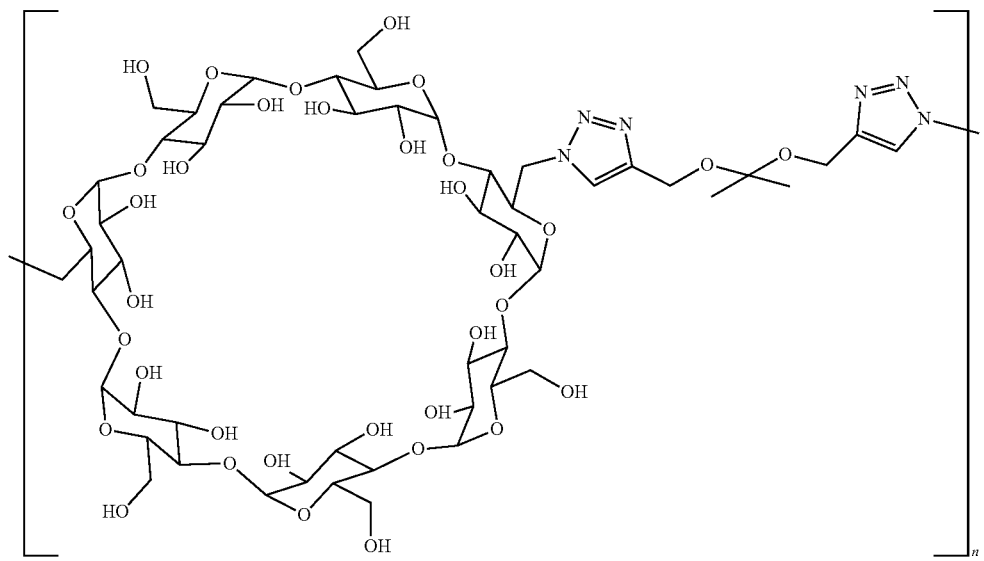

wherein n is from 4 to 1000.

7. The method of claim 6, wherein:
(a) n is from 10 to 100;
(b) n is from 10 to 75; or
(c) n is from 15 from 65.

8. The method of claim 6, wherein n is about 17.

9. The method of claim 6, wherein n is about 25.

10. The method of claim 1, wherein the cyclodextrin polymer is administered in a pharmaceutical composition further comprising a pharmaceutically acceptable excipient.

11. The method of claim 10, the pharmaceutical composition further comprising one or more additional therapeutically active agents.

12. The method of claim 11, the one or more additional therapeutically active agents comprising one or more angiotensin-converting enzyme inhibitors selected from the group consisting of captopril, zofenopril. enalapril, ramipril, quinapril, perindopril, lisinopril, benazepril, imidapril, trandolapril, cilazapril, and fosinopril.

13. The method of claim 11, the one or more additional therapeutically active agents comprising one or more angiotensin receptor blockers selected from the group consisting of azilsartan, candesartan, eprosartan, irbesartan, losartan, olmesartan, telmisartan, sparsentan, and valsartan.

14. The method of claim 1, wherein the kidney glomerular disease is selected from the group consisting of Focal Segmental Glomerulosclerosis, Alport Syndrome, Diabetic Kidney Disease, Minimum Change Kidney Disease, Minimum Change Nephropathy, glomerulonephritis, glomerulosclerosis, podocyte affected diseases, and combinations thereof.

15. The method of claim 1, wherein the cyclodextrin polymer is administered by a route selected from intramuscular, intraperitoneal, intravenous (systemic), subcutaneous, transdermal, oral, rectal, inhalation, topical, and intranasal.

16. The method of claim 1, wherein the cyclodextrin polymer is administered at a dose ranging from about 10 mg/kg/day up to about 200 mg/kg/week.

17. A method for reducing lipid content in a cell or plasma membrane of a cell in a patient suffering from a kidney glomerular disease, the method comprising administering to the patient in need thereof, an effective amount of the cyclodextrin polymer having the following structure:

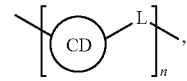

wherein
CD is a cyclodextrin moiety or a derivative thereof;
L is a linker moiety, wherein L comprises the following structure:

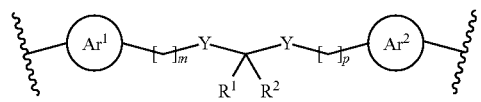

wherein $Ar^1$ and $Ar^2$ are each independently a 5- or 6-membered heteroaryl comprising 1, 2, 3 or 4 heteroatoms individually selected from N, O, and S, wherein $Ar^1$ and $Ar^2$ are optionally substituted with 1 to 3 $R^3$ groups;
Y is independently O, S, or $NR^4$;
m and p is each independently an integer from 1 to 10;
$R^1$ and $R^2$ are each independently $R^4$, $OR^4$, $SR^4$ or $R^1$ and $R^2$ taken together with the carbon atom to which they are attached form a double bonded O, S, or $NR^4$;
$R^3$ is selected from the group consisting of H, $C_1$-$C_3$ alkyl, $C_1$-$C_3$ alkyl sulfide, hydrazine, amine and halogen; and
$R^4$ is H or a saturated or unsaturated $C_1$-$C_{10}$ linear alkyl, saturated or unsaturated $C_1$-$C_{10}$ branched alkyl, or saturated or unsaturated $C_1$-$C_{10}$ cycloalkyl, each of which is optionally substituted; and
n is from 4 to 1000.

18. The method claim 1, wherein the mean blood urea nitrogen level in a subject afflicted with kidney glomerular disease after treatment is substantially similar to the level in a subject not afflicted with a kidney glomerular disease and having normal kidney function.

19. The method of claim 1, wherein the mean albumin to creatinine ratio in a subject afflicted with kidney glomerular disease after treatment is substantially similar to the ratio in a subject not afflicted with a kidney glomerular disease and having normal kidney function.

* * * * *